US011420003B2

(12) United States Patent
Amarasinghe

(10) Patent No.: US 11,420,003 B2
(45) Date of Patent: Aug. 23, 2022

(54) SUPPLEMENTAL GAS DELIVERY DEVICE FOR MASK ASSEMBLY

(71) Applicant: ResMed Pty Ltd, Bella Vista (AU)

(72) Inventor: Amal Shirley Amarasinghe, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 691 days.

(21) Appl. No.: 16/185,163

(22) Filed: Nov. 9, 2018

(65) Prior Publication Data

US 2019/0076613 A1 Mar. 14, 2019

Related U.S. Application Data

(63) Continuation of application No. 14/099,485, filed on Dec. 6, 2013, now Pat. No. 10,155,096, which is a (Continued)

(30) Foreign Application Priority Data

Feb. 19, 2010 (AU) ................................ 2010900710

(51) Int. Cl.
*A61M 16/06* (2006.01)
*A61M 16/08* (2006.01)

(52) U.S. Cl.
CPC ........ *A61M 16/0666* (2013.01); *A61M 16/06* (2013.01); *A61M 16/065* (2014.02); (Continued)

(58) Field of Classification Search
CPC .......... A61M 16/0057; A61M 16/0078; A61M 16/0463; A61M 16/06; A61M 16/0605; A61M 16/0611; A61M 16/0622; A61M 16/0633; A61M 16/065; A61M 16/0655; A61M 16/0666; A61M 16/0672; A61M 16/0683; A61M 16/0816; A61M 16/0825; A61M 16/0858; A61M 2202/0208; (Continued)

(56) References Cited

U.S. PATENT DOCUMENTS 690,663 A 1/1902 Pratt
1,362,766 A 12/1920 McGargill
(Continued)

FOREIGN PATENT DOCUMENTS

WO WO 2004/052438 6/2004
WO WO 2006/122092 11/2006
WO WO 2008/031149 3/2008

*Primary Examiner* — Annette Dixon
(74) *Attorney, Agent, or Firm* — Nixon & Vanderhye P.C.

(57) ABSTRACT

A supplemental gas delivery device is described for a mask assembly having at least one supplemental gas port, the at least one supplemental gas port including an aperture in communication with an interior of the mask assembly. The mask assembly may include an aperture communicating with an interior of the mask assembly, and a cannula for communicating with the supplemental gas port. The cannula is positioned to deliver supplemental gas adjacent to the patient's nares and/or mouth, to increase an efficacy of treatment for the patient by more directly applying the flow of supplemental gas to the patient's nares. An optional bridging portion may be included to provide a connection between supplemental gas port and the cannula.

25 Claims, 19 Drawing Sheets

Related U.S. Application Data continuation of application No. 13/030,812, filed on Feb. 18, 2011, now Pat. No. 8,616,209.

(52) U.S. Cl.
CPC .... *A61M 16/0611* (2014.02); *A61M 16/0622* (2014.02); *A61M 16/0672* (2014.02); *A61M 16/0858* (2014.02)

(58) Field of Classification Search
CPC .. A61M 2205/3331; A61M 2210/0618; A61M 2210/1053; A61M 2230/005; A61M 16/01; A61M 16/0459; A61M 16/0488; A61M 16/08; Y10S 128/912; Y10S 128/26; Y10T 137/9247
See application file for complete search history.

(56) References Cited

U.S. PATENT DOCUMENTS

| | | | |
|---|---|---|---|
| 1,873,160 A | 8/1932 | Sturtevant | |
| 2,178,800 A | 11/1939 | Lombard | |
| 2,663,297 A | 12/1953 | Turnberg | |
| 4,201,205 A | 5/1980 | Bartholomew | |
| 4,231,363 A | 11/1980 | Grimes | |
| 4,248,218 A | 2/1981 | Fischer | |
| 4,263,908 A | 4/1981 | Mizerak | |
| 4,328,797 A * | 5/1982 | Rollins, III | A61M 16/06 128/202.15 |
| 4,354,488 A | 10/1982 | Bartos | |
| 4,367,735 A | 1/1983 | Dali | |
| 4,454,880 A | 6/1984 | Muto et al. | |
| 4,706,683 A | 11/1987 | Chilton | |
| 5,005,571 A | 4/1991 | Dietz | |
| 5,348,000 A * | 9/1994 | Teves | A61M 16/06 128/204.18 |
| 5,400,781 A | 3/1995 | Davenport | |
| 5,465,712 A | 11/1995 | Malis | |
| 5,474,060 A | 12/1995 | Evans | |
| 5,560,354 A | 10/1996 | Berthon-Jones et al. | |
| 6,439,230 B1 | 8/2002 | Gunaratnam et al. | |
| 6,571,798 B1 | 6/2003 | Thornton | |
| 6,581,601 B2 | 6/2003 | Ziaee | |
| 6,626,177 B1 | 9/2003 | Ziaee | |
| 6,644,315 B2 | 11/2003 | Ziaee | |
| 6,679,257 B1 | 1/2004 | Robertson et al. | |
| 6,820,617 B2 | 11/2004 | Robertson et al. | |
| 7,195,018 B1 | 3/2007 | Goldstein | |
| 7,255,107 B1 | 8/2007 | Gomez | |
| 8,136,527 B2 | 3/2012 | Wondka | |
| 8,616,209 B2 | 12/2013 | Amarasinghe | |
| 10,155,096 B2 * | 12/2018 | Amarasinghe | A61M 16/065 |
| 2002/0157672 A1 | 10/2002 | Gunaratnam | |
| 2003/0024533 A1* | 2/2003 | Sniadach | A61M 16/06 128/205.25 |
| 2007/0113856 A1 | 5/2007 | Acker et al. | |
| 2007/0144525 A1 | 6/2007 | Davidson et al. | |
| 2007/0175533 A1 | 8/2007 | Herron | |
| 2008/0066757 A1* | 3/2008 | Stallard | A61M 16/0057 128/205.25 |
| 2008/0295846 A1 | 12/2008 | Han et al. | |
| 2009/0211574 A1* | 8/2009 | Sniadach | A61M 16/0459 128/200.26 |
| 2010/0051034 A1 | 3/2010 | Lynch et al. | |
| 2011/0203591 A1 | 8/2011 | Amarasinghe | |
| 2013/0060157 A1 | 3/2013 | Beard | |
| 2014/0096773 A1 | 4/2014 | Amarasinghe | |

* cited by examiner

SUPPLEMENTAL GAS DELIVERY DEVICE FOR MASK ASSEMBLY

CROSS REFERENCE TO PRIORITY APPLICATION

This application is a continuation of U.S. application Ser. No. 14/099,485, filed Dec. 6, 2013, now U.S. Pat. No. 10,155,096, which is a continuation of U.S. application Ser. No. 13/030,812, filed Feb. 18, 2011, now U.S. Pat. No. 8,616,209, which claims the benefit of Australian Provisional Application No. 2010900710, filed Feb. 19, 2010, each of which is incorporated herein by reference in its entirety.

FIELD OF THE INVENTION

The invention relates to a supplemental gas delivery device for a mask assembly used for Non-invasive Positive Pressure Ventilation (NPPV) and for continuous positive airway pressure (CPAP) therapy of sleep disordered breathing (SDB) conditions such as obstructive sleep apnea (OSA), and to a mask assembly including the supplemental gas delivery device.

BACKGROUND OF THE INVENTION

Mask assemblies used in the treatment of SDB may comprise a nasal mask, designed to fit over a patient's nose, nasal prongs interfacing with a patient's nose, or a full face mask designed to fit over the nose and mouth of the patient. In both cases, the mask may be held in position by headgear.

The mask generally comprises a relatively rigid shell, termed a frame, which defines a rearwardly opening cavity covering the patient's nose and/or mouth and a soft portion, termed a cushion, which contacts and seals against the patient in a preferably comfortable manner.

The air or other breathable gas is supplied by a blower and passed along a flexible conduit to the mask, with the mask frame having a gas inlet that communicates with the conduit.

In addition to the gas inlet, the mask may also have $CO_2$ washout vents and one or more small diameter ports through which supplemental gas such as oxygen may be introduced or through which pressure or other measurements may be made. The ports typically comprise one or more cylindrical connectors molded into the mask frame, usually projecting outwards e.g., forward or downward, from the front surface of the exterior portion of the frame. The mask ports typically also include a cap which may be inserted into or over the ports when the ports are not in use to prevent leakage of air from the mask. Depending on the part construction and the relative diameters of the ports and the tubing which supplies supplemental oxygen, the ports may function as a male or a female connector.

The ports may be provided in alternative locations, such as above, below or on sides of the primary gas inlet and elbow assembly, and there may be one port or more than one port. For example, the Mirage® nasal mask (ResMed Ltd.) is a generally triangular mask with a gas inlet tube connected to an elbow assembly on the front of the mask. The two ports of that mask are located just below the elbow assembly connecting the primary gas inlet and generally adjacent the patient's upper lip region.

When a supplemental gas such as supplemental oxygen is applied through the ports, the gas is delivered to an interior of the mask through the ports, which may not be positioned as close as possible to the patient's nasal region. The location of the ports may thus reduce the effectiveness of delivery of the supplemental gas to the patient as the supplemental gas may escape through the vents or through a leak in the seal between the cushion and the patient's face before the supplemental gas can be delivered to the patient.

SUMMARY OF THE INVENTION

One aspect of the invention relates to a supplemental gas delivery device for a mask assembly having at least one supplemental gas port, the at least one supplemental gas port including an aperture communicating with an interior of the mask assembly, and a cannula for communicating with the supplemental gas port. The cannula is positioned to deliver supplemental gas adjacent to the patient's nares and/or mouth, to increase an efficacy of treatment for the patient by more directly applying the flow of supplemental gas to the patient's nares and/or mouth. An optional bridging portion may be included to provide a connection between the supplemental gas port and the cannula.

Another aspect of the invention relates to a mask assembly including a frame having a primary gas delivery inlet and a supplemental gas delivery port, and including the supplemental gas delivery device.

Another aspect of the invention relates to a mask assembly having a supplemental gas delivery device, wherein the supplemental gas delivery device is positioned proximal to the patient's airways.

Another aspect of the invention relates to a mask assembly having a supplemental gas delivery device, wherein the supplemental gas delivery device is positioned proximal to the patient's nares.

Another aspect of the invention relates to a mask assembly having a supplemental gas delivery device, wherein the supplemental gas delivery device is positioned proximal to the patient's mouth.

Another aspect of the invention relates to a mask assembly having a supplemental gas delivery device, wherein the supplemental gas delivery device is movable to be proximal to the patient's nares or the patient's nose.

Another aspect of the invention relates to a mask assembly having a supplemental gas delivery device, wherein the supplemental gas delivery device is positioned proximal to the patient's nose and mouth.

Another aspect of the invention relates to a mask assembly having a supplemental gas delivery device, wherein the supplemental gas delivery device is positioned proximal to the patient's nares and not within the patient's nares, and/or proximal to the patient's mouth and not within the patient's mouth.

In an alternative, a supplementary gas delivery device may extend to and possibly (slightly) within the patient's nares and/or mouth, but does not contact and/or form a seal with the patient's nose and/or mouth.

Another aspect of the invention relates to a mask assembly having a supplemental gas delivery device, wherein the supplemental gas delivery device is positioned proximal to the patient's nares and/or mouth, for example within about 50 mm of the patient's nares and/or mouth.

Another aspect of the invention relates to a mask assembly having a supplemental gas delivery device, wherein the supplemental gas delivery device is positioned proximal to the patient's nares and/or mouth, for example within about 30 mm of the patient's nares and/or mouth.

Another aspect of the invention relates to a mask assembly having a supplemental gas delivery device, wherein the supplemental gas delivery device is positioned proximal to the patient's nares and/or mouth, for example within about 10 mm of the patient's nares and/or mouth.

Another aspect of the invention relates to a mask assembly having a supplemental gas delivery device, wherein the supplemental gas delivery device is positioned proximal to the patient's nares and/or mouth, for example within about 5 mm of the patient's nares and/or mouth.

According to another aspect of the invention there is provided a supplemental gas delivery device for a mask assembly having at least one supplemental gas port, the at least one supplemental gas port including an aperture in communication with an interior of the mask assembly, e.g., extending from an exterior of the mask assembly to the interior of the mask assembly, the supplemental gas delivery device including a bridging portion adapted to be insertable into or over the supplemental gas port, the bridging portion when inserted including a connection portion extending out of the supplemental gas port into the interior of the mask assembly, and at least one cannula having a first end and a second end, the first end adapted to communicate with the connection portion of the bridging portion, and the second end being positioned adjacent to the patient's nares and/or mouth to direct the flow of the supplemental gas through the bridging portion and the cannula to the patient's nares and/or mouth.

According to another aspect of the invention there is provided a mask assembly including a frame having a primary gas delivery inlet and at least one supplemental gas port, the at least one supplemental gas port including an aperture communicating with an interior of the mask assembly, e.g., extending from an exterior of the mask assembly to the interior of the mask assembly, a bridging portion adapted to be insertable into the supplemental gas port, the bridging portion when inserted including a connection portion extending out of the supplemental gas port into the interior of the mask assembly, and at least one cannula having a first end and a second end, the first end adapted to communicate with the connection portion of the bridging portion, and the second end being positioned adjacent to the patient's nares and/or mouth to direct the flow of the supplemental gas through the bridging portion and the cannula to the patient's nares and/or mouth.

According to another aspect of the invention there is provided a mask assembly including a frame having a primary gas delivery inlet and a pair of supplemental gas ports, the pair of supplemental gas ports each including an aperture communicating with an interior of the mask assembly, e.g., extending from an exterior of the mask assembly to the interior of the mask assembly, a pair of bridging portions, each bridging portion extending into a respective one of the supplemental gas ports, the bridging portions each including a first portion having an outer diameter substantially equal to a diameter of the aperture, and a second portion having a diameter greater than the first portion, the first portion of the bridging portions each including a connection portion extending out of the supplemental gas ports and into the interior of the mask assembly, the second portions having a shoulder interfacing with the supplemental gas ports on the outside of the mask assembly, and a pair of cannulas each having a first end and a second end, the first end connected to the connection portion of the bridging portions, and the second end being positioned adjacent to a patient's nares and/or mouth in use, to maximize the flow of the supplemental gas through the bridging portion and the cannula to the patient's nares and/or mouth.

According to another aspect of the invention there is provided a cannula having a first end being insertable into or over a supplemental gas port of a mask assembly, and a second end being positioned within the mask assembly and adjacent to a nasal area and/or mouth area of a patient in use, wherein supplemental gas is deliverable through the cannula to the patient's nasal area and/or mouth area.

According to another aspect of the invention there is provided a mask assembly including a frame having a primary gas delivery inlet and at least one supplemental gas port, the at least one supplemental gas port including a portion extending into an interior of the mask assembly, and a cannula having a first end and a second end, the first end adapted to communicate with the portion of the supplemental gas port extending into an interior of the mask assembly, and the second end being positioned within the mask assembly and adjacent to a nasal area and/or mouth area of a patient in use, wherein supplemental gas is deliverable through the cannula to the patient's nasal area and/or mouth area.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 7-1 to 7-9 show schematic cross sectional views of nasal cannulae according to examples of the present technology;

FIG. 8 is a cross-sectional view of the supplemental gas delivery device of FIG. 7;

FIG. 9 is a partial cross-sectional view of the supplemental gas delivery device of FIG. 7;

DETAILED DESCRIPTION OF ILLUSTRATED EMBODIMENTS

The following includes a description of a supplemental gas delivery device, and of mask assemblies including or retrofitted with such a supplemental gas delivery device according to embodiments of the present invention. In the illustrated embodiments, the supplemental gas delivery device is adapted to be removably attached to a frame or other portion of a mask assembly. However, in alternative embodiments the device may be permanently attached or otherwise integrally formed with the frame.

Mask Assembly

Figure 1:
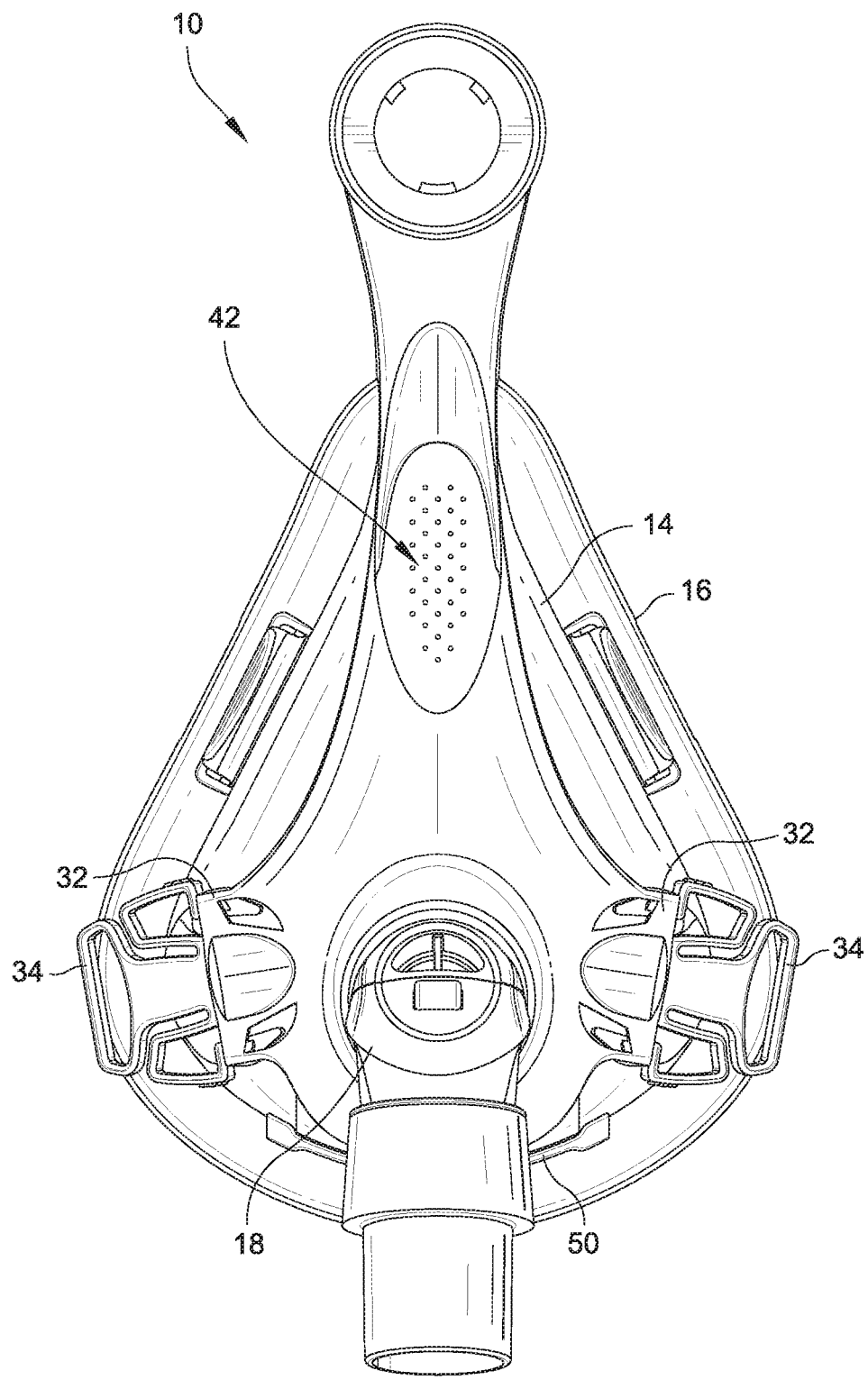
FIG. 1 is a front view illustrating a full facial mask.
Figure 2:
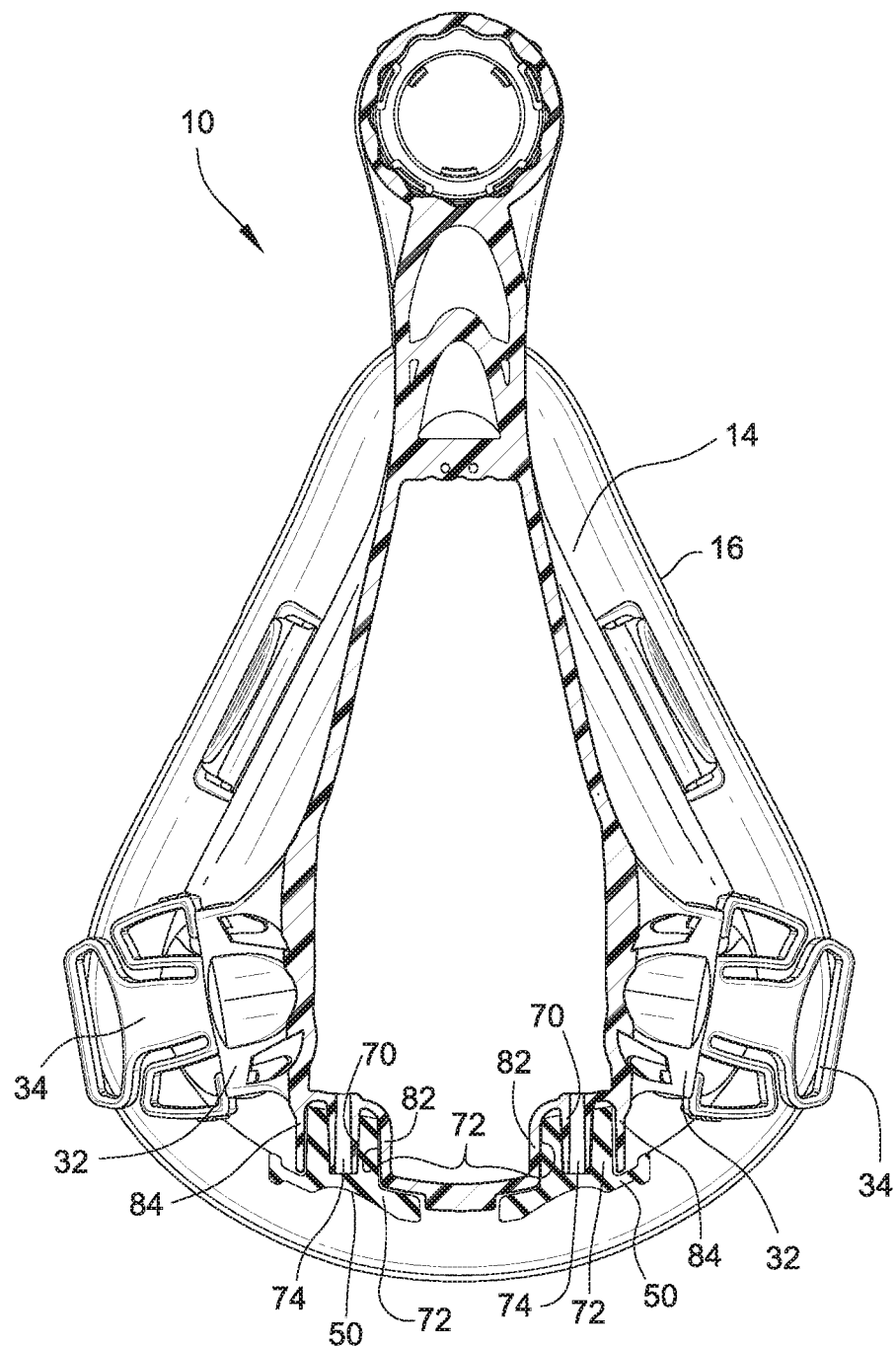
FIG. 2 is a cross-sectional view of the full facial mask of FIG. 1 and showing a cap covering the ports.

FIGS. 1 and 2 illustrate an exemplary embodiment of a known mask assembly 10. As illustrated, the mask assembly 10 includes a frame 14, a cushion 16 provided to the frame 14 and adapted to form a seal with the patient's face, an elbow assembly 18 provided to the frame 14 and adapted to be connected to an air delivery tube (not shown) that delivers breathable gas to the patient, lower headgear clip receptacles 32 adapted to be engaged with clips 34, a vent assembly 42 for gas washout, and a ports cap 50. The ports cap 50 may be removably attached to one or more ports when the ports are not in use, as further explained below. A forehead support (not shown) may be provided to the frame, and headgear (not shown) may be removably attached to the frame 14 and forehead support to maintain the mask assembly 10 in a desired adjusted position on the patient's face.

Further details and embodiments of such mask assembly are disclosed in U.S. Published Application No. 2010-0051034, published May 5, 2009 and entitled "Frame and Vent Assembly For Mask Assembly", which is incorporated herein by reference in its entirety.

As shown in the cross-sectional view of FIG. 2, the frame 14 includes two ports 70 located respectively in recesses 72 in the base or lower portion of the frame 14. These recesses 72 are positioned in between the lower headgear clip receptacles 32. The ports 70 are provided so that in use, supplemental oxygen or other breathable gas can be delivered into the breathing cavity of the main assembly by connecting a supplemental gas supply to the ports 70. Each port 70 is formed as a tubular spigot that forms a male connector on the outside of the mask onto which small bore tubing supplying, for example, supplemental oxygen, may be attached. Alternatively, the ports 70 may be used to measure pressure in the breathing cavity, and means for measuring the pressure inside the mask may be attached to the ports 70. When the ports 70 are not in use, the ports cap 50 is inserted onto the ports 70, interfacing and sealing with the male connector to provide a seal.

In the illustrated embodiment, each recess 72 is bounded by one or more walls, e.g., an inner side wall 82 and an outer side wall 84, and is open at its bottom end. A front wall may be formed as a continuation of a front wall portion of the frame 14. The walls 82 and 84 of the recess 72 are spaced from the port 70 by a sufficient distance to allow a small bore oxygen tube to be pushed onto the port 70, and also to allow the ports cap 50 to be received therewithin when the port 70 is not in use. Each port 70 includes an aperture 74 defining a passageway extending along a length of the port 70 to an inner portion of the mask.

Supplemental Gas Delivery Device

According to an embodiment of the invention, a supplemental gas delivery device 43 may be connected to one or both of the ports 70 to deliver supplemental gas closer to the patient's nares and/or mouth so as to more directly or effectively deliver supplemental gas to the patient. The supplemental gas delivery device 43 is shaped and positioned inside the mask assembly 10 so that the outlet of the device will be positioned as close to the patient's airways as possible to maintain the flow of the supplemental gas to the patient. The device may be formed to address the needs of a mouth breather, a nose breather, or a nose and mouth breather (e.g., separate branches to nares and mouth).

In an example, the supplemental gas delivery device 43 may be positioned proximate the patient's airways. For example, the supplemental gas delivery device 43 may be positioned close or adjacent to the patient's nares so that when the patient breathes in through their nose, he receives additional oxygen. Alternatively, the supplemental gas delivery device 43 may be positioned close or adjacent to the patient's mouth so that when the patient breathes in through their mouth, he receives additional oxygen. In a further alternative, the supplemental gas delivery device 43 may be positioned proximate or adjacent both the patient's nose and mouth to ensure that the patient receives additional oxygen regardless of whether he breathes through their nose or their mouth. In a further alternative, the supplemental gas delivery device 43 may be movable from a first position to a second position such that the first position is proximate the patient's nares and the second position is proximate the patient's mouth.

In an example, the supplemental gas delivery device 43 may be positioned proximal or close to the patient's nares to increase the volume of oxygen to the patient's airways. The supplemental gas delivery device 43 may be positioned within 50 mm of the patient's airways, e.g., the supplemental gas delivery device 43 may be positioned within 30 mm of the patient's airways; the supplemental gas delivery device 43 may be positioned within 10 mm of the patient's airways; the supplemental gas delivery device 43 may be positioned within 5 mm of the patient's airways. By providing the device close to the airways, the amount of supplemental gas (e.g., $O_2$) that is inhaled can be increased.

For example, for a nose breather, the amount of gas, e.g., $O_2$, breathed in by the patient can be greater than 22%, e.g., up to about 30-38% or more (e.g., 40-50%),—compared to the same mask provided without a cannula, depending on proximity of the end of the cannula to the patient's nose, based on 12 cm $H_2O$ pressure, at a flow rate of 63 L/min and a supplemental gas flow rate of 7 L/m. For a mouth breather under similar pressure and flow conditions, the patient inhaled greater than 21% of the supplemental gas, e.g., between 27%-29% or more depending on how close the cannula were placed to the patient's mouth. The gas delivery device in examples does not seal within and does not extend into the patient's airways (nose/mouth). In other examples, the gas delivery device does not contact and/or does not form a seal with the patient's nose and/or mouth, although it may be inserted slightly within the patient's airways.

The supplemental gas delivery device 43 includes at least one hollow tube-like portion, or cannula 45, with an opening formed at each end and a hollow interior extending between the ends for conveying the supplemental gas.

Figure 3:
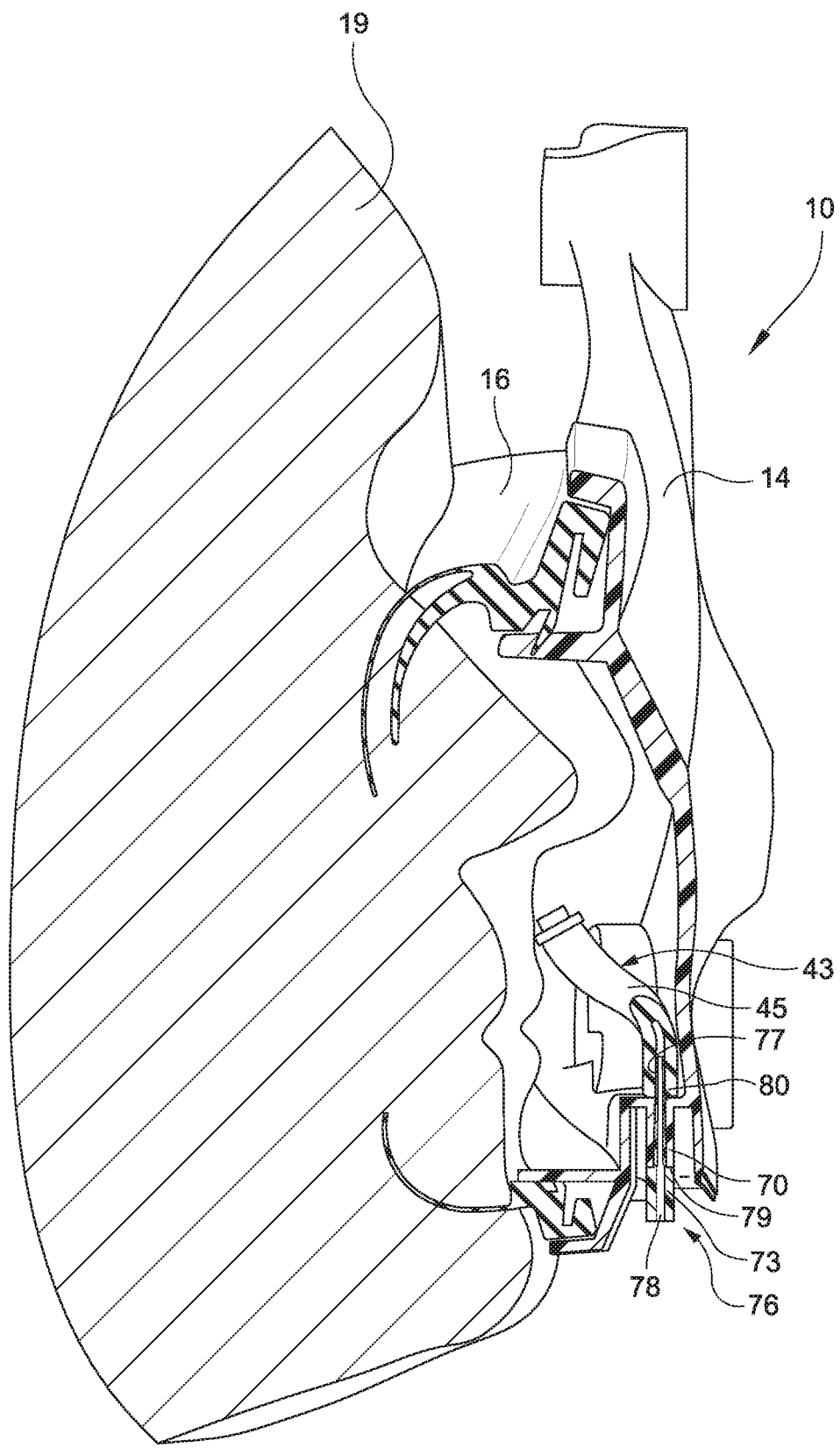
FIG. 3 is a cross-sectional side view of the full facial mask of FIG. 1 and showing a supplemental gas delivery device provided to the ports according to an embodiment of the present invention.
Figure 4:
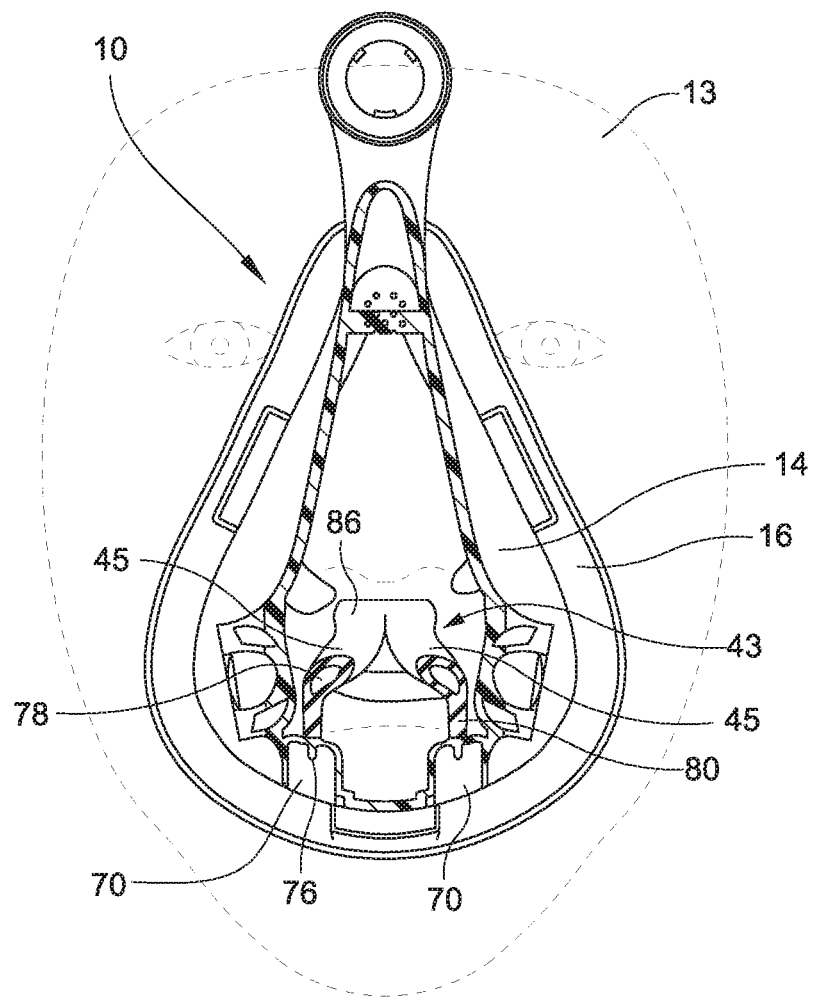
FIG. 4 is another cross-sectional view showing the full facial mask and supplemental gas delivery device of FIG. 3.
Figure 5:
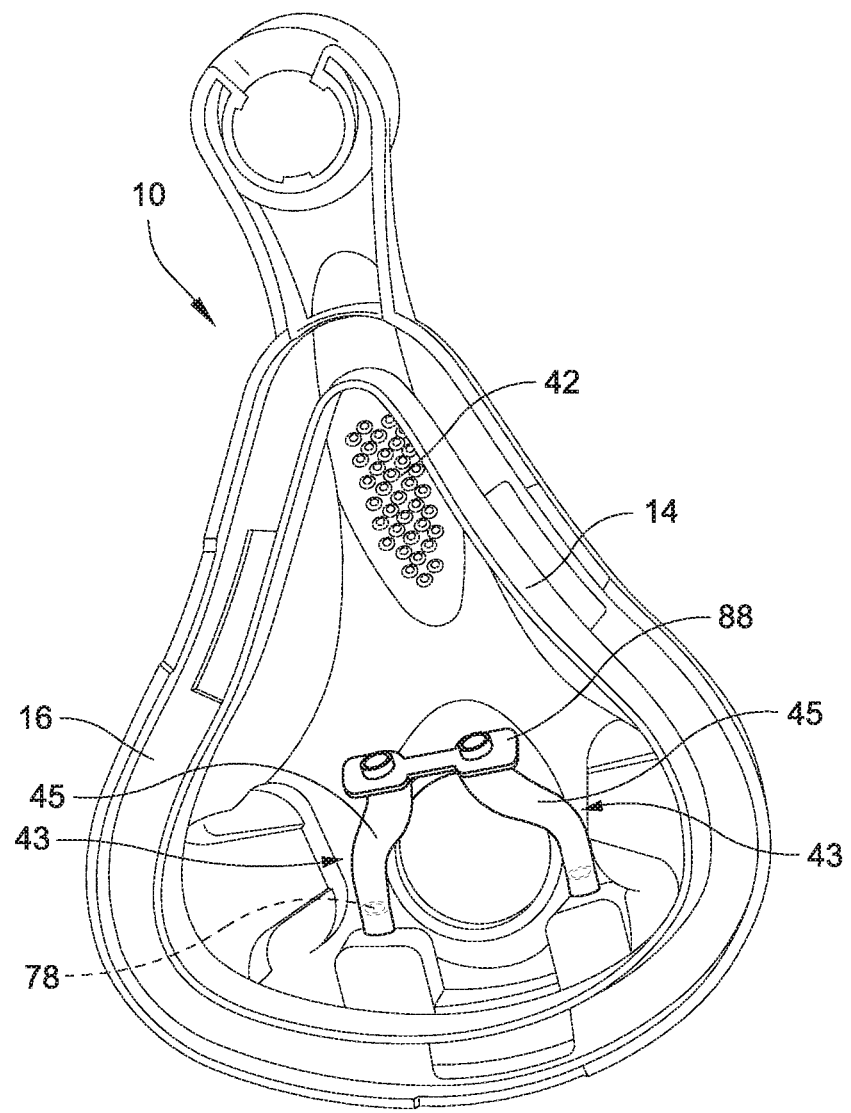
FIG. 5 is a rear view showing a full facial mask assembly and supplemental gas delivery device.
Figure 6:
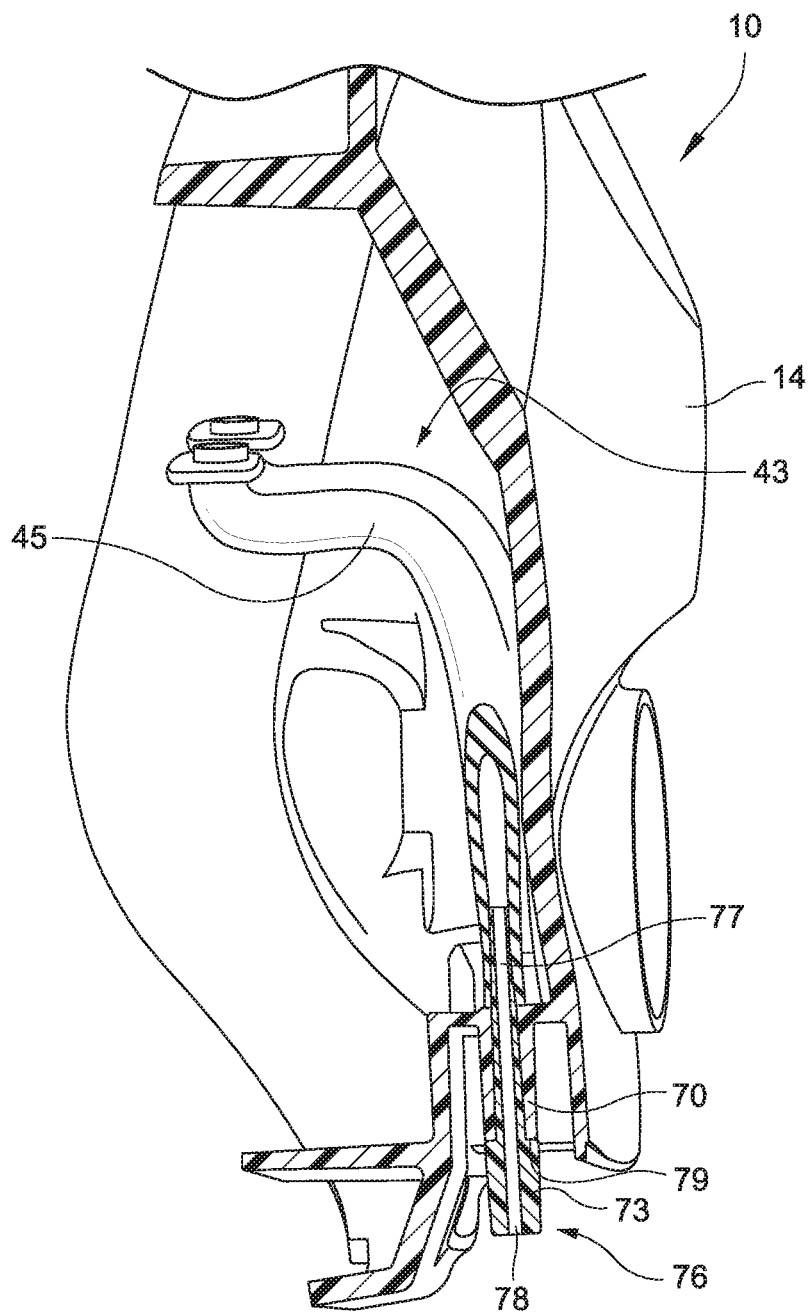
FIG. 6 is an enlarged cross-sectional view showing the full facial mask and supplemental gas delivery device of FIG. 5.
Figure 7:
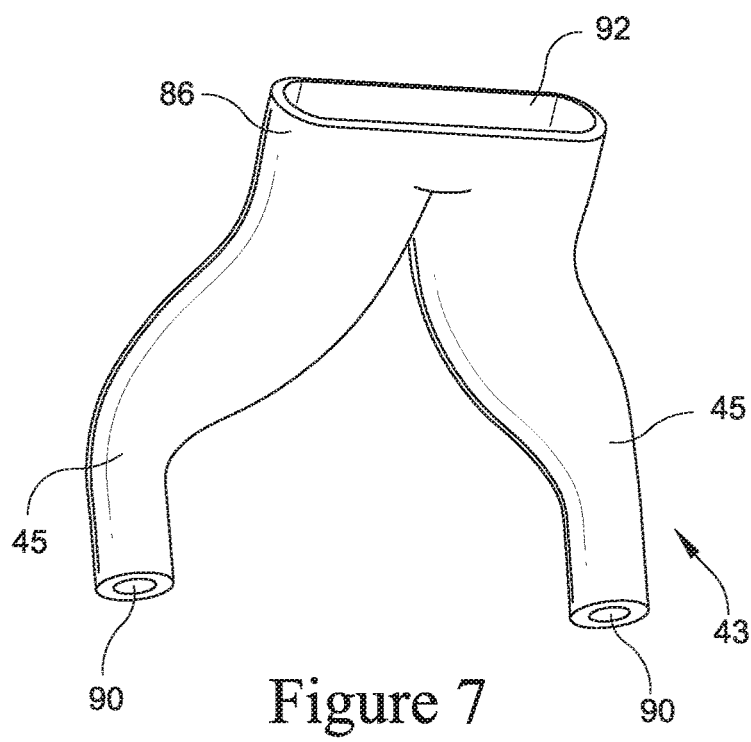
FIG. 7 is a perspective view illustrating a supplemental gas delivery device according to an embodiment of the present invention.
Figures 1, 7:
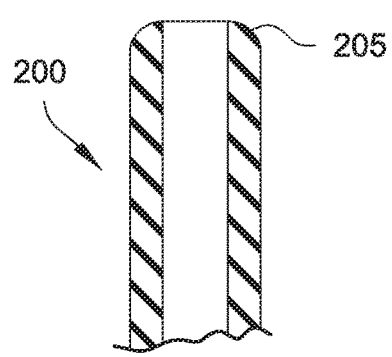
Figures 2, 7:
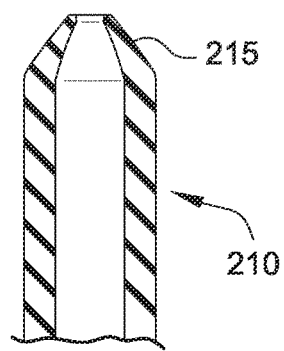
Figures 3, 7:
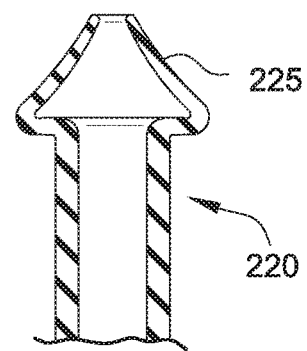
Figures 4, 7:
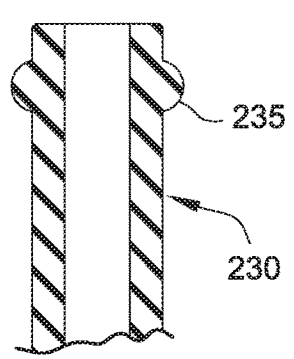
Figures 5, 7:
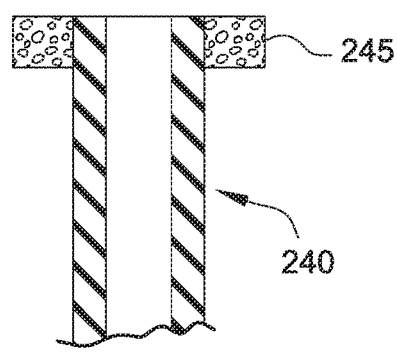
Figures 6, 7:
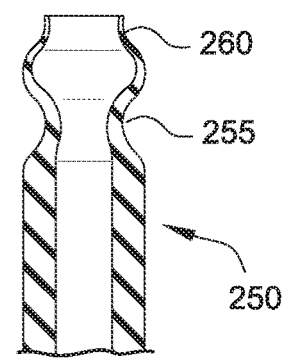
Figure 7:
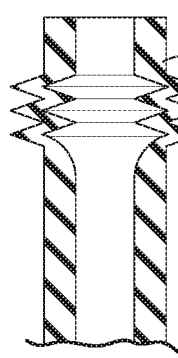
Figures 7, 8:
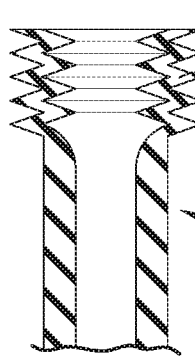
Figures 7, 8, 9:
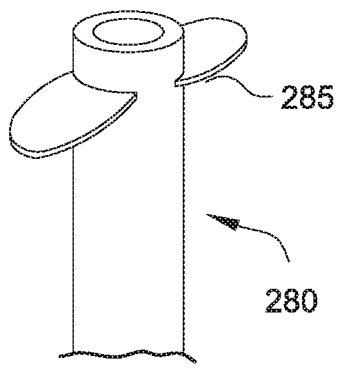
Figure 8:
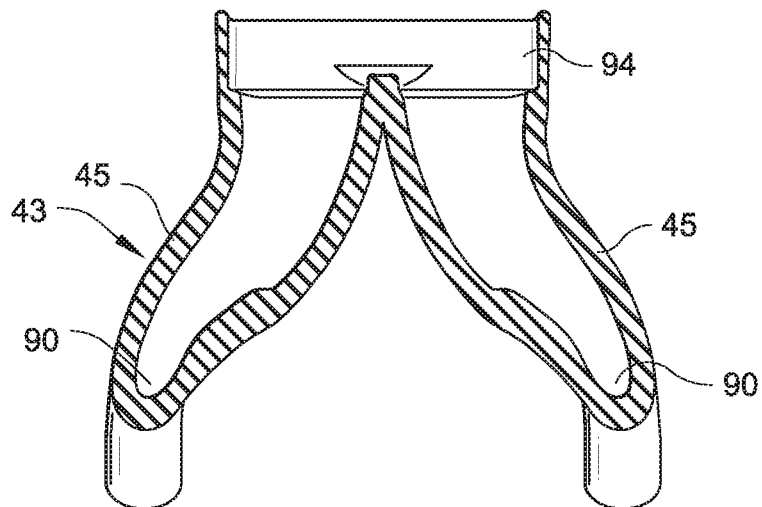
Figure 9:
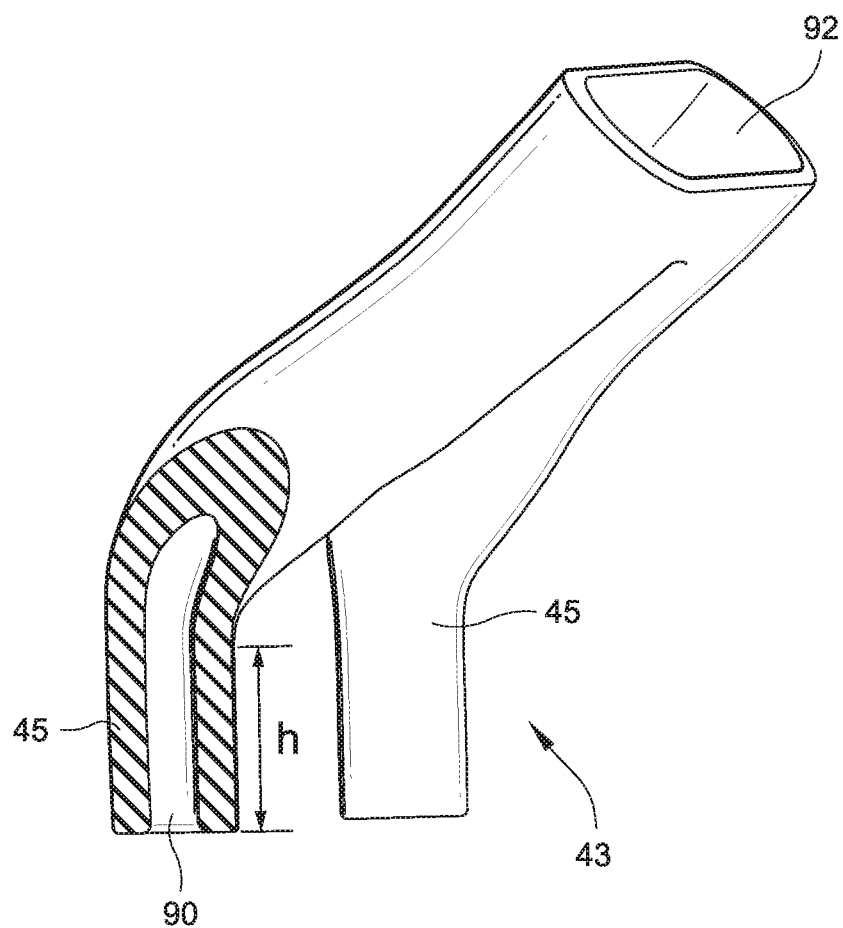

FIGS. 7-1 to 7-9 show schematic cross sections of cannulae variants according to the present technology. As described above, each of these cannula may be placed in close proximity to the patient's nose and/or mouth, e.g. within about 50 mm, but may also be slightly inserted into the nose, perhaps even with some degree of sealing. FIG. 7-1 shows a cannula 200 with a radiused tip 205 that faces the patient. The tip of the cannula may include or made of a softer material compared to the remainder of the cannula, or the entire cannula can be made of such softer material. FIG. 7-2 shows a cannula 210 with a tapered tip, which tapered tip 215 may have a wall thickness that also varies, e.g., thinner towards the distal end. FIG. 7-3 shows a cannula 220 with a cone shaped tip 225 (a locating feature), e.g., a nozzle, puff or prong. FIG. 7-4 discloses a cannula 230 with a bead 235 at or near its tip. FIG. 7-5 shows a cannula 240 with a (co-molded) foam portion 245 at or near its tip. The foam portion may be inserted into the patient's nose, to positively locate the cannula in a comfortable manner. The foam portion is compressible and has a large porosity allowing a gas to pass there through, between the nose wall and the cannula wall. In addition, or in the alternative, the cannula wall may have a certain degree of porosity (e.g., one or more holes) allowing the gas from the mask chamber to pass into the cannula. FIG. 7-6 discloses a cannula 250 having a notch 255 to receive the inside rim of the nare, and a tapered tip 260 having a thinner or more compliant cross section. FIG. 7-7 discloses a cannula 360 having a gusset section 365 to allow angular and/or length adjustment, like a "drinking straw". This may be an advantage in fitting the mask, e.g., by first locating the cannula relative to the nares, and then fitting the overall mask to seal against the patient's nose/mouth, which may entail length-wise compression of the cannulae accommodated by the gusset/concertina section. FIG. 7-8 shows a cannula 270 with a concertina section 275 at or near the tip to dampen or soften any contact between the patient's nose and the cannula tip. FIG. 7-9 shows a cannula 280 with one or more flanges 285 that are spaced a distance 290 from the end of the cannula, to limit insertion depth of the cannula, somewhat like the bridging portion 88 in FIG. 5. The flanges allow chamber gas to pass into the patient's nose.

In an embodiment, the cannula 45 may be attached to or molded with a malleable wire or the like to allow the patient to bend or adjust the position of the cannula. The malleable wire can provide the cannula with additional support, while still allowing the cannula to be flexible. The cannula 45 may thus be flexible and malleable, allowing the cannula 45 to be bent or adjusted from a first position or configuration to stay in a second position or configuration.

The cannula 45 may be molded or otherwise formed from various materials, such as silicone, thermoplastic elastomer, foam, gel, polypropylene, polycarbonate, metal, or any other suitable material. The cannula 45 may be provided in several sizes, or may be one long tube that can be cut, e.g., with scissors, and/or may include pre-scored portions, so that the mask can be fit with a cannula 45 that comes closest to the patient's nares/mouth. Also, the supplemental gas delivery device 43 may be used with a variety of different masks (as discussed below), and an appropriately sized supplemental gas delivery device 43 could then be selected for the mask being used.

The supplemental gas delivery device 43 may be over molded or otherwise formed with the mask assembly.

The supplemental gas delivery device 43 may be formed to connect to any number of ports on a mask assembly, and will generally include one cannula 45 for each port present on the mask, although less than all of the ports on a mask could be utilized. In the illustrated embodiments, the device include one or more cannulas 45, each including a first end portion or inlet communicated with a respective port 70 (e.g., via a bridging portion 76 as described below) and a second end portion or outlet adapted to be positioned near the patient's nares. As illustrated, a bridging member or link may interconnect the outlets, e.g., to maintain proper spacing between the outlets. In addition, the link may provide a widened platform, e.g., see FIG. 5, to provide a stop for substantial insertion of the cannulas into the patient's nares in use.

Figure 12A:
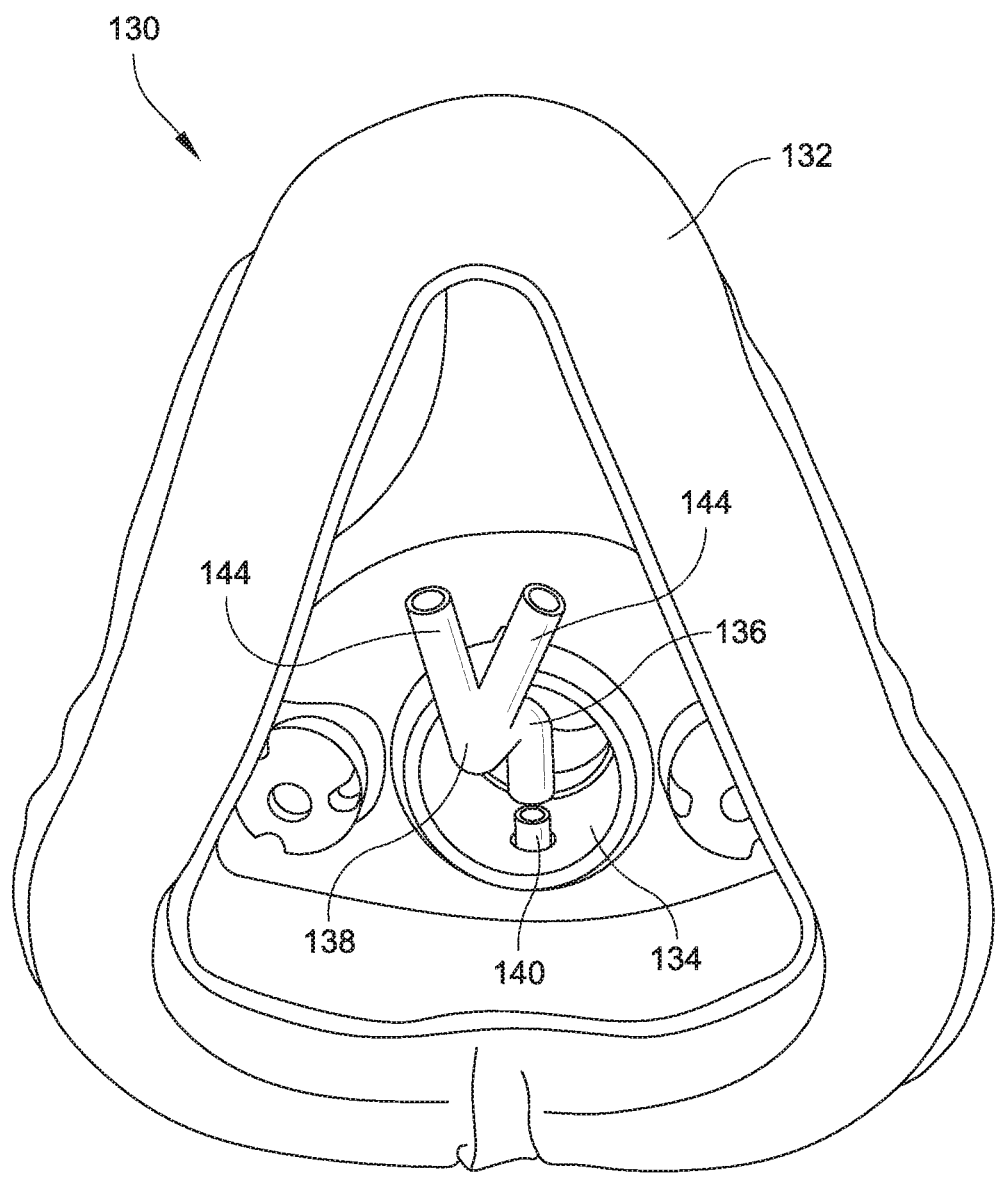
FIG. 12A is a rear perspective view of a known full facial mask assembly retrofitted with a supplemental gas delivery device according to an embodiment of the present invention.

In an alternative embodiment, as shown in FIGS. 7-9, the two cannulas 45 may converge to form a single outlet for delivering the supplemental gas, or they may diverge to provide individual supply of supplemental gas dedicated for each nare, e.g., such as illustrated in FIG. 12A.

In each embodiment, the cannula 45 may taper along its length, e.g., a diameter of the cannula enlarges from inlet to outlet. However, other suitable arrangements are possible, e.g., a constant diameter. The cannula 45 may be positioned close to the patient's nares, preferably within 5 mm. The cannula 45 is preferably flexible so that if it contacts the patient, it will not cause discomfort or irritation.

One or more reinforcing features may be provided to the cannula 45 to prevent accidental occlusion, i.e., features structured to maintain cannula 45 in open position, for example, one or more internal ribs or other anti-crush structure.

Bridging Portion/Nipple

On many existing mask assemblies (such as the mask assembly shown in FIGS. 1 and 2), the outlet of the port 70 on the inside of the mask may be flush with an inner surface of the frame and contain no provision for attaching the supplemental gas delivery device 43, such as a male connector or the like. Accordingly, the supplemental gas delivery device 43 may include one or more nipples or bridging portions 76, as best shown in FIGS. 3 and 6. As illustrated, the bridging portion 76 is in the form of a hollow tube. The bridging portion is adapted to be insertable into the aperture 74 in the port 70, to extend at least partly through the aperture 74 in the port, and to provide a connecting portion extending out of the aperture 74 on an inside of the mask assembly 10. The bridging portion 76 may be insertable either from an inside of the mask assembly 10, or from an outside of the mask assembly 10. The bridging portion 76 may be formed from plastic rubber, or other suitable material. A shape and/or a diameter of the bridging portion 76 may be selected to match the shape and/or diameter of the aperture 74 of the port 70.

Then the bridging portion 76 may be adapted to be inserted into the aperture 74 in the port 70, and to extend beyond the port 70 both inside the mask assembly and outside the mask assembly 10 (e.g., see FIG. 3), or may extend beyond the port 70 only on the inside of the mask assembly 10 and not on an outside of the mask assembly 10. The portion of the bridging portion 76 adapted to extend inside the mask assembly is utilized to connect to the tube-like cannula 45 of the supplemental gas delivery device 43 on the inside of the mask assembly 10.

The inlet of the cannula 45 has a inner diameter selected to be substantially the same (or slightly smaller) than the outer diameter of the cannula connecting portion 77 of the nipple 76 that extends inside the mask assembly 10 beyond the port 70, to allow the cannula 45 of the supplemental gas delivery device 43 to be fitted (e.g., press-fitted) over the portion of the nipple 76. The cannula connecting portion 77 may taper along its length to facilitate insertion into the cannula.

In the illustrated embodiment, the bridging portion may include a wide portion or base 73 that is wider than the cannula connecting portion 77. The portion extending through the port and into the mask interior has an outer diameter substantially the same or slightly narrower than the diameter of the aperture 74 in the port 70, so that it may be press-fit into aperture 74. The base 73 has an outer diameter that is larger than the outer diameter of the cannula connecting portion 77, and provides a shoulder 79 that can interface or abut with an outer edge of the port 70 when the nipple 76 is inserted into the aperture 74 in the port 70. The base 73 may have an outer diameter that is the same as the outer diameter of the male connector of the port 70, to allow a standard supplemental gas tube to be attached to the base. The base 73 may be gripped by a user when inserting or removing the bridging portion 76 from the port 70. The base 73 will act as a stop to prevent the bridging portion 76 from going completely inside the mask. In some of the embodiments described herein, the wide portion or base 73 is omitted, but the base 73 may optionally be included on any of the embodiments described herein.

The bridging portion 76 includes a hole 78 that traverses the entire length of the bridging portion 76, and may have a constant diameter, although a varying diameter could also be used. When the bridging portion is inserted into the aperture 74 in the port 70, and a supply of supplemental gas (not shown) is connected to the bridging portion 76, for example at the base 73, the supplemental gas can be transported through the hole 78 to the cannula 45 of the supplemental gas delivery device 43.

Connection and Operation

FIGS. 3, 5, and 6 show the mask assembly 10 having two ports 70 connected to the supplemental gas delivery device 43. As illustrated, the supplemental gas delivery device 43 has two cannulas 45 connecting to respective ports 70 via the bridging portions 76. The diameter of the holes 78 may be constant from the bridging portion connecting portions 80 running the length of the cannulas 45 to an end portion 86 to be disposed adjacent to the patient 13 nares in use, or the diameter may increase or decrease along the length of the cannulas 45. FIG. 4 illustrates the cannulas 45 of FIGS. 7-9 connecting to respective ports. As illustrated in FIG. 5, the cannulas 45 may be connected to an optional bridge portion 88 at an end of the cannulas 45 that will be positioned adjacent to the patient's 13 nares in use. The bridge portion 88 holds the ends of the cannulas 45 apart a predetermined distance. A plurality of bridge portions of different widths may be provided, which may allow the selection of an appropriate width for the patient 13. Any of the embodiments described herein may include the bridge portion 88.

FIG. 7 illustrates a supplemental gas delivery device 43 in further detail. The supplemental gas delivery device 43 in this embodiment includes two cannulas 45, each having an exit hole 90 formed in their ends for connecting to the bridging portions 76, with the holes extending a length of the interior of the cannulas 45 to the end portion 86, to be disposed adjacent to the patient's nares. The diameter of the exit holes 90 may increase from a smallest diameter at the ends to be connected to the bridging portions 76 along a length of the cannulas 45, as illustrated in the cross-sectional view of FIG. 8. The cannulas 45 connect to each other at the end portion 86 to be disposed adjacent to the patient's nares, and may form one exit aperture 92 for delivering the supplemental gas to the patient. The supplemental gas delivery device 43 may include structure 94 to reinforce or maintain the device in an open position at the end adjacent to the patient's nares.

As illustrated in the cross-sectional view of FIG. 9, the diameter of the interior of the cannulas 45 may be substantially constant for a predetermined distance h extending from the exit holes 90 to accommodate the bridging portion 76 in a snug fit and to prevent leakage of the supplemental gas. The diameter of the holes in the interior of the cannulas 45 may increase and/or decrease after the distance h towards the exit hole 90, or may remain constant. The interior diameter is at about 1 mm, or at least about 1 mm, e.g., the diameter is at least about 3 mm, although larger diameters are possible, e.g., 4 mm, 5 mm or more.

Retrofit to Existing Mask Assemblies

Preferably, the device may be retrofit to pre-existing mask systems. Numerous mask assemblies are described below that may be retrofitted with the supplemental gas delivery device according to embodiments of the present invention. All of the embodiments may include any of the supplemental gas delivery device features described above.

In all of the embodiments, the cannula may include a cannula hole that has a constant diameter along an entire length of the cannula, or has a diameter that increases or decreases along the length of the cannula. In embodiments utilizing the bridging portion, the cannula hole may have a diameter sized to fit over the bridging portion (having a diameter substantially the same, or slightly greater than, the outer diameter of the bridging portion), and in embodiments where the cannula fits into the supplemental gas port aperture, the outer diameter of the cannula may be substantially the same, or slightly less than, the diameter of the aperture of the supplemental gas port. In all of the embodiments utilizing a bridging portion fit into the aperture in the supplemental gas port, the outer diameter of the bridging portion will be substantially the same as (or slightly less than) the diameter of the aperture of the supplemental gas port.

Figure 10:
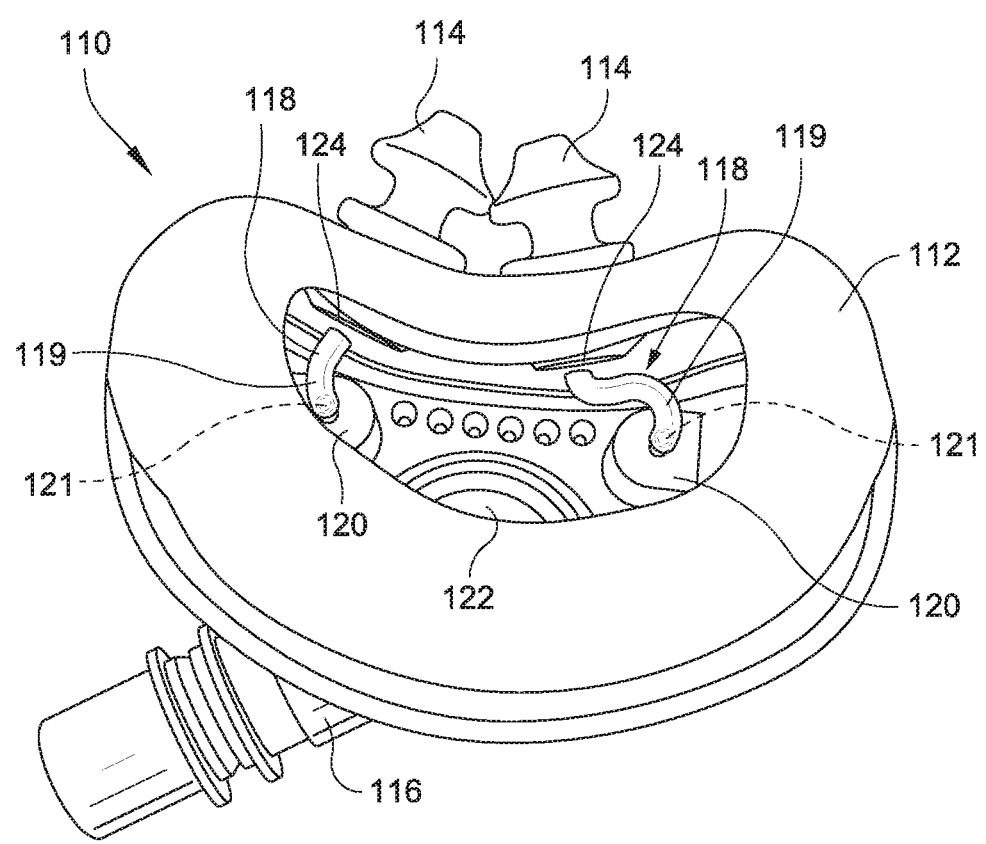
FIG. 10 is a rear perspective view illustrating of a known full facial mask that seals individually at the mouth and nose retrofitted with a supplemental gas delivery device according to an embodiment of the invention.
Figure 11:
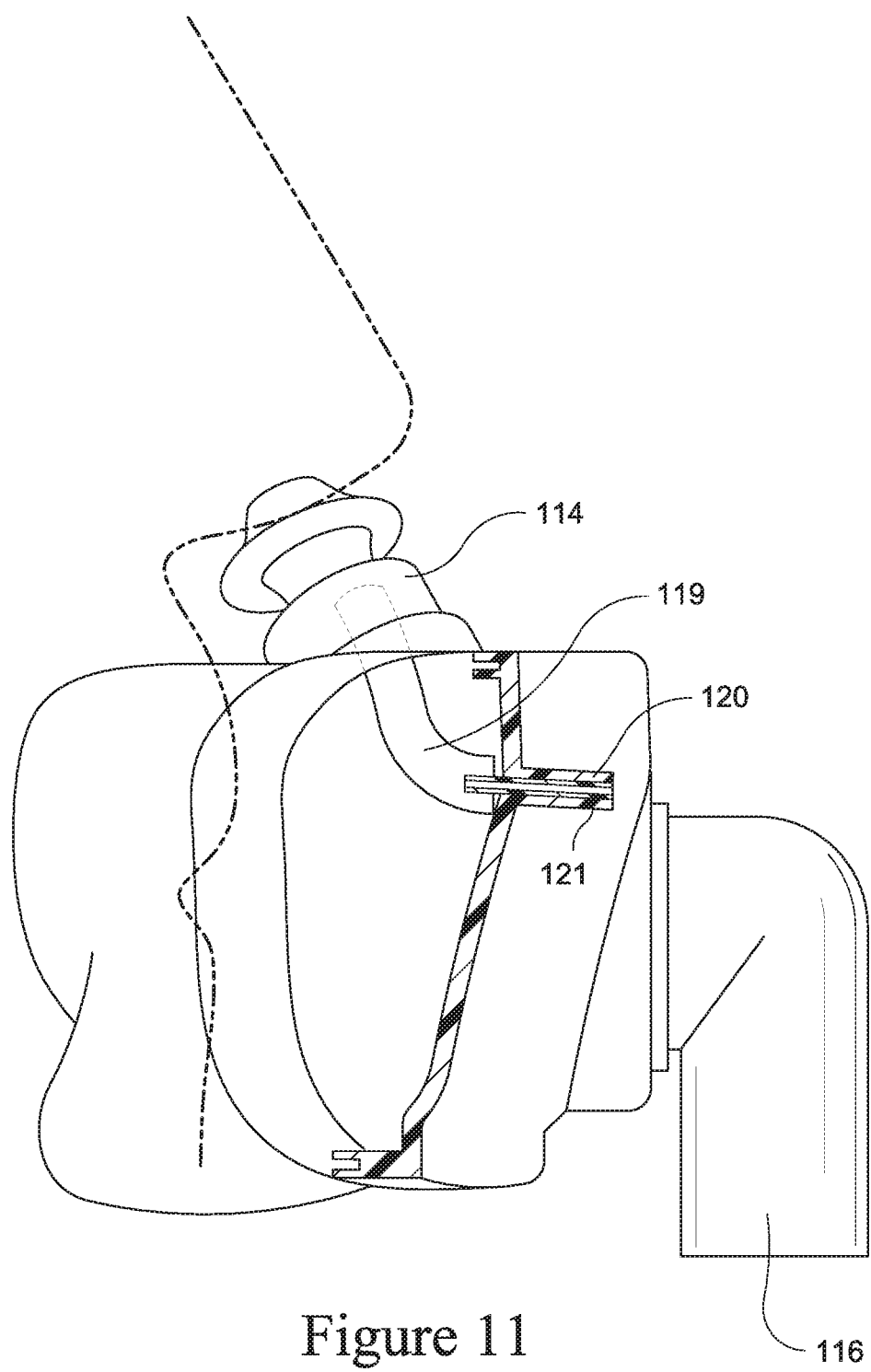
FIG. 11 is a cross-sectional view of the full facial mask of FIG. 10.

FIGS. 10 and 11 illustrate a known mask 110 (commercially sold as the Respcare Hybrid™ mask) that seals individually at the mouth and nose. The mask 110 includes a cushion 112 for interfacing and sealing with a mouth region, nasal prongs 114 for interfacing with a nasal region, and an elbow connector 116 for connecting to a supply of gas. The mask 110 may be equipped or retrofitted with a supplemental gas delivery device 118 according to an embodiment of the invention. In the illustrated mask 110, two supplemental gas delivery ports 120 are present. The opening 122 in the face of the mask is connected to the primary supply of gas, typically by the elbow connector 116. The supplemental gas delivery ports 120 are located on both sides and slightly above the opening 122.

The supplemental gas delivery device 118 that may be retrofitted to the mask 110 includes two cannulas 119 connected to respective ports 120 via bridging portions 121. The cannulas 119 are positioned and shaped to deliver supplemental gas close to the inlet openings 124 in the nasal prongs 114 on the inside of the mask 110, and the supplemental gas is then conveyed through the nasal prongs 114 to the nares of the patient. The cannulas 119 may also be positioned and shaped to deliver supplemental gas inside the inlet openings 124 in the nasal prongs 114 on the inside of the mask 110, as illustrated in FIG. 11. The cannulas 119 of the supplemental gas delivery device 118 may be fitted over the portion of the bridging portions 121 extending out of the ports 120. The bridging portions 121 are not needed if the ports 120 include a male connector extending into the interior of the mask 110. The cannulas 119 may be pre-shaped for this mask 110, or may be adjustable to be fitted by a user, e.g., the two cannulas 119 may be malleable so the user may bend them into position.

Figure 13A:
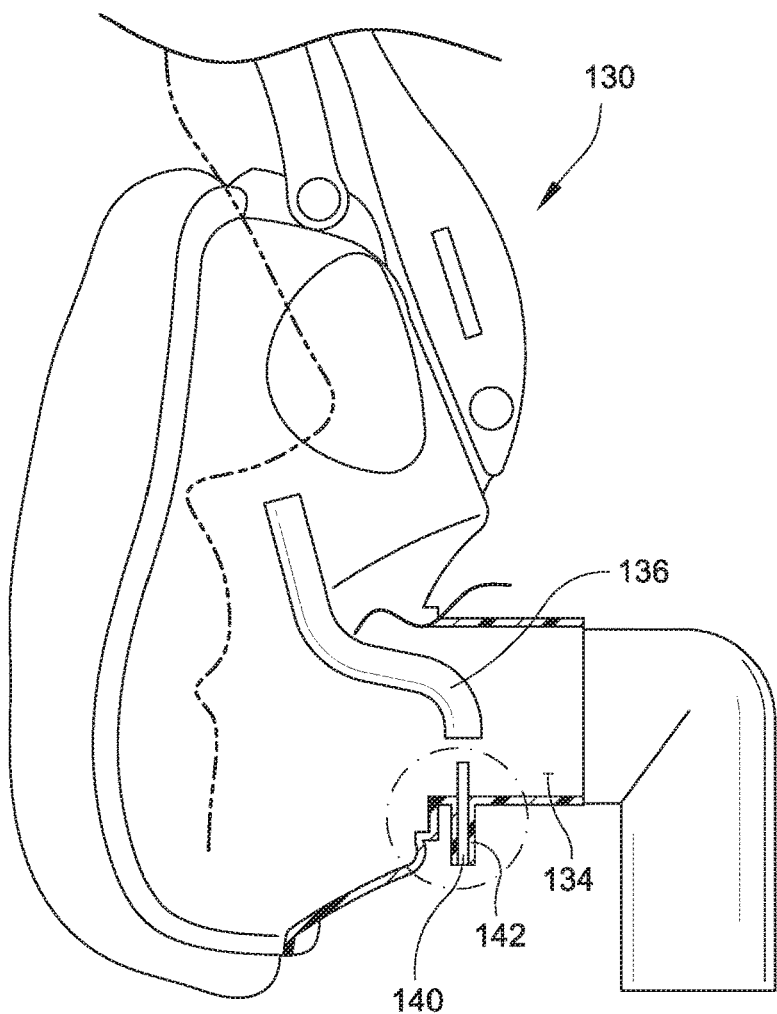
FIG. 13A is an enlarged cross-sectional view of the full facial mask assembly of FIG. 12A.

FIG. 12A illustrates a known mask 130 (commercially sold as the Sleepnet Mojo™ mask) that includes a cushion 132 and an inlet tube 134 for delivery of primary breathable gas into the interior of the mask 130. This mask includes a port 142, as illustrated in the cross-sectional view of FIG. 13A, positioned on the inlet connector 134. The port 142 interfaces with the mask 130 via inlet connector 134.

The mask 130 may be equipped or retrofitted with a supplemental gas delivery device 138. The supplemental gas delivery device 138 may include a bridging portion 140 fitted into the port 142 and extending into an opening of the inlet connector 134, and a cannula 136 fitted over the bridging portion 140. In this embodiment, the supplemental gas delivery device 138 may include a cannula that splits or bifurcates into two tube-like outlet portions 144, one placed adjacent each nare of a patient in use. However, this embodiment could be modified to use a single opening adjacent the patient's nares, such as illustrated in FIG. 7. The supplemental gas delivery device 138 may be shaped with a bend to extend out of the opening of the inlet connector 134, and then have an additional bend to extend upward towards the patient's nares. The supplemental gas delivery device 138 may be flexible and bendable into such a position by a patient.

Figure 12B:
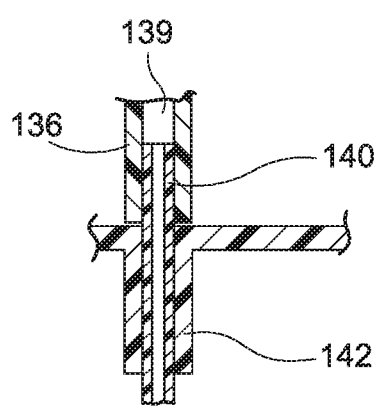
FIG. 12B is an enlarged cross-sectional view illustrating the port, bridging portion and cannula of FIG. 12A, in which the cannula is connected.
Figure 13B:
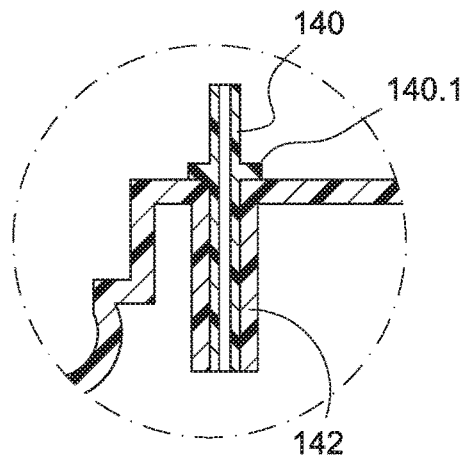
FIG. 13B is an enlarged cross-sectional view of an alternative embodiment of the supplemental gas delivery device of FIG. 13A.

FIG. 12B illustrates an enlarged cross-sectional view of the port 142, the bridging portion 140 and the cannula 136, with the cannula fitted onto the bridging portion 140. As illustrated, the diameter of hole 139 is substantially the same as (or slightly larger than) the outer diameter of the portion of the bridging portion 140 that extends out of the opening of the inlet connector 134, to provide a snug fit when the cannula 136 is fit on the bridging portion 140. FIG. 13B shows a similar cross-sectional view as FIG. 12B, with the cannula 136 not fitted onto the bridging portion 140. FIG. 13B shows the bridging portion 140 to include an integrally formed shoulder 140.1, to limit the insertion depth to of the bridging portion to a predetermined length, to which the cannula 136 is attached. The shoulder 140.1 may abut against an inner edge of the port 142 on an inside of the mask assembly. In this embodiment, the bridging portion 140 is inserted into the port 142 from inside the mask assembly. The cannula 136 may then be fitted over the bridging portion 140.

Figure 13C:
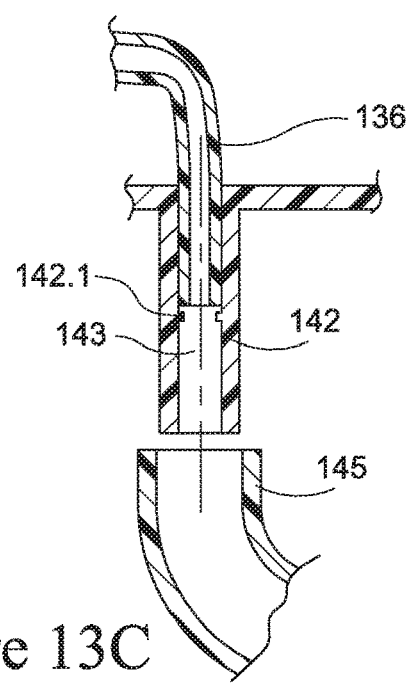
FIG. 13C is an enlarged cross-sectional view of an alternative embodiment of the supplemental gas delivery device of FIG. 13A.

FIG. 13C shows an alternative embodiment, in which the bridging portion is not used, and the cannula 136 is fit into the hole or aperture 143 in the port 142. In this embodiment, the outer diameter of the cannula is substantially the same as the diameter of the aperture 143 in the port 142. This embodiment may include step 142.1 formed in the aperture 143, which will allow the cannula 136 to be inserted a predetermined distance into the aperture 143 from inside the mask assembly. Step 142.1 may also form a stop if the hose 145 is inserted into rather than over port 142. A mask assembly could be retrofit with such a cannula 136 fit into aperture 143, or the mask assembly could initially be made to include the cannula fit into hole 143. Further, the cannula 136 and port 142 could be formed from a unitary construction, such that the cannula 136 is not removable from the aperture 143 of port 142.

Figure 13D:
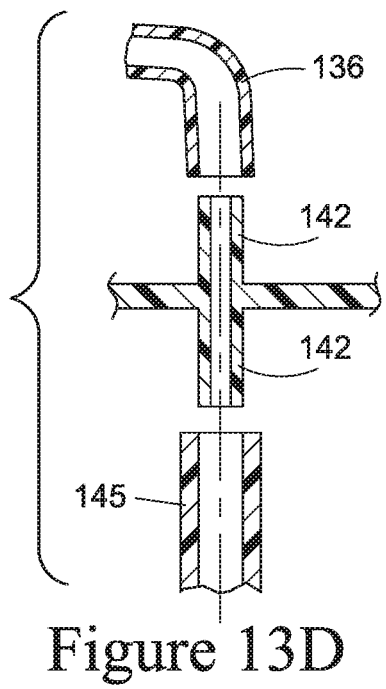
FIG. 13D is a is an enlarged cross-sectional view of an alternative embodiment of the supplemental gas delivery device of FIG. 13A.

FIG. 13D shows a port 142 that protrudes inside the mask assembly. In this embodiment, the cannula 136 may be fit over the portion of the port 142 that protrudes inside the mask assembly, and the supplemental gas hose 145 may be connected to the portion of the port 142 that protrudes on an outside of the mask assembly.

Figures 13E, 13F:
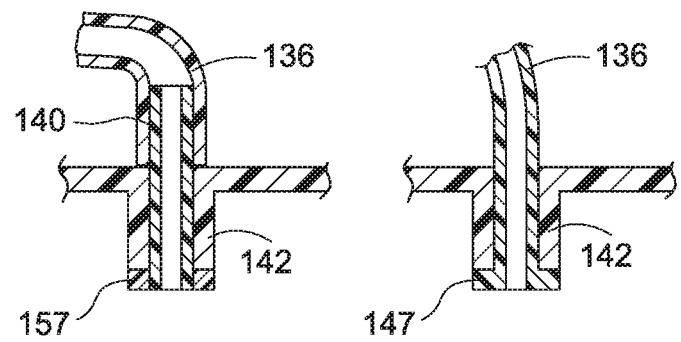
FIG. 13E is a is an enlarged cross-sectional view of an alternative embodiment of the supplemental gas delivery device of FIG. 13A.
FIG. 13F is a is an enlarged cross-sectional view of an alternative embodiment of the supplemental gas delivery device of FIG. 13A.

FIG. 13E shows an embodiment in which bridging portion 140 is preassembled or formed in one piece with the cannula 136. The shoulder of the cannula defines the insertion depth of the bridging portion. Such preassembly can be achieved by various methods, including adhesives, welding, ultrasonic welding, soldering, etc. The bridging portion is inserted into the port 142. Bridging portion may include surface treatment or features (e.g., splines) to enhance the connection between the bridging portion and the inside of the port. In addition, a fixing member 157 may be connected to the bridging portion 140 to ensure the bridging portion and cannula assembly does not become detached inside the mask assembly. The fixing member 157 abuts against an outer edge of the supplemental gas port. The fixing member may be connected to the bridging portion 140 by any means, such as by glue or another adhesive, or by mechanical means such as a bayonet fitting, detents, threaded nut, etc., or the like. The outer profile of the fixing member 157 can match the outer profile of the port 142, so that a supplemental gas hose may be fit over both the fixing member 157 and the port 142.

FIG. 13F illustrates an embodiment in which the cannula 136 is inserted into the aperture in the port 142, and a bridging portion is not utilized. In this embodiment, the cannula 136 is inserted from the outside of the mask into the aperture in the port 142. A shoulder 147 is included on the cannula, and the shoulder 147 may abut against an outer edge portion of the port 142. The shoulder 147 prevents the cannula from entering into and becoming detached on the inside of the mask assembly. Shoulder 147 has an outer profile that matches the shape of the port, to allow connection of the hose 145.

Figure 14:
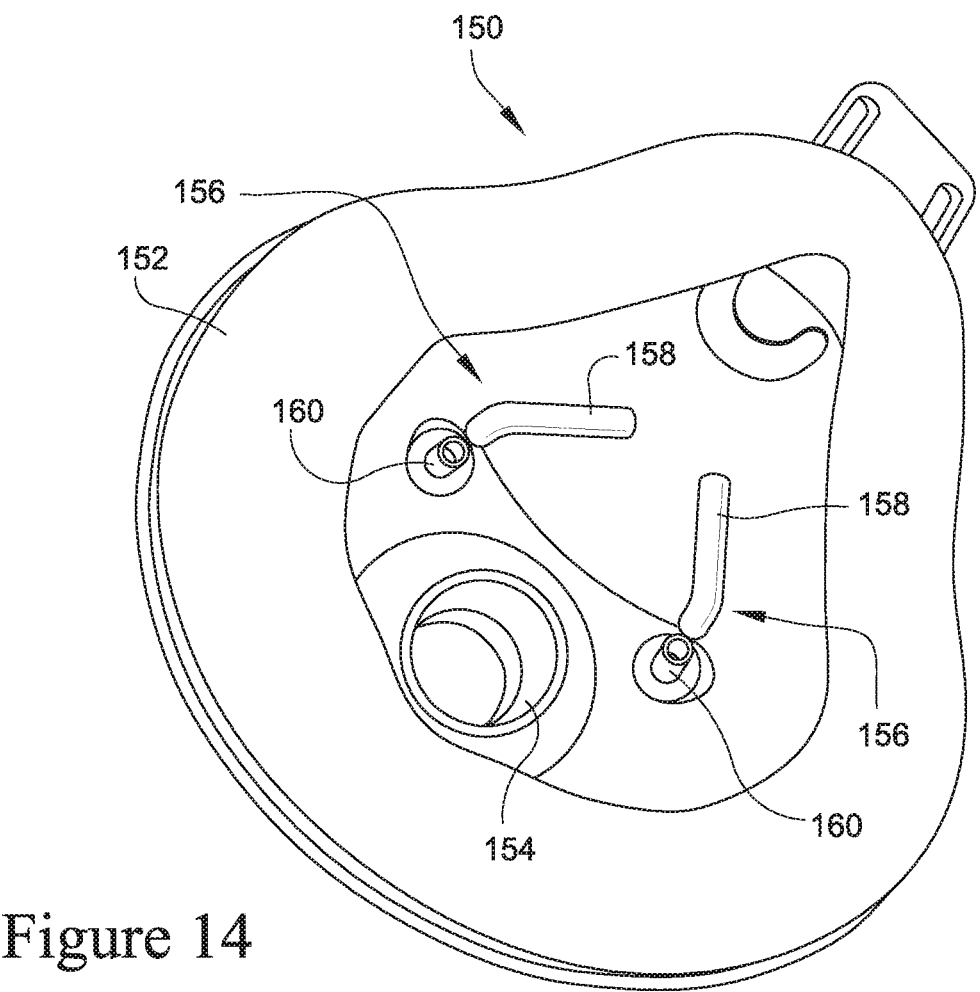
FIG. 14 is a rear perspective view of a known full facial mask assembly retrofitted with a supplemental gas delivery device according to an embodiment of the present invention.
Figure 15:
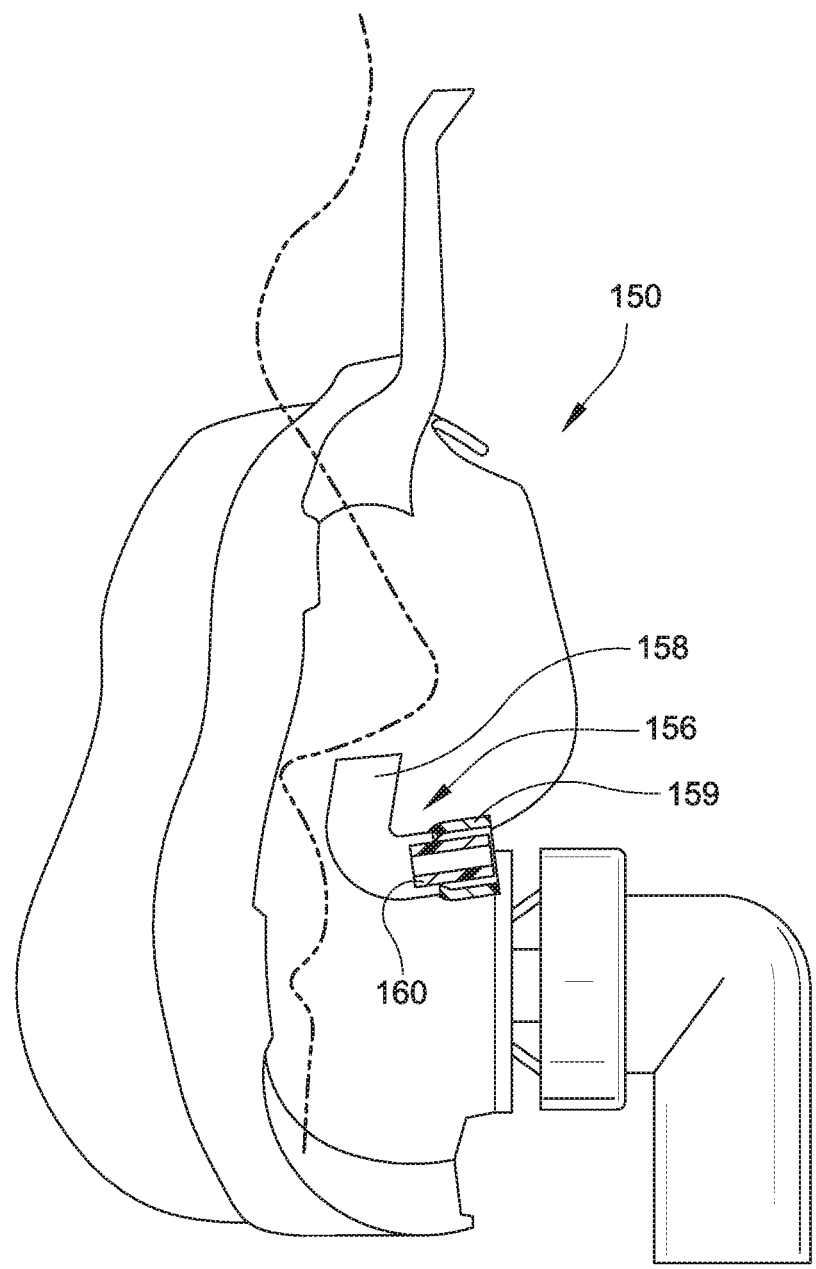
FIG. 15 is a cross-sectional view of the full facial mask assembly of FIG. 14.

FIG. 14 illustrates a known mask 150 (commercially sold as the ResMed Mirage™ full face mask) that includes a cushion 152 and an opening 154 for delivery of primary breathable gas into the interior of the mask 150. This mask includes two ports 159, as illustrated in the cross-sectional view of FIG. 15, positioned on both sides and slightly above the opening 154.

The mask 150 may be equipped or retrofitted with a supplemental gas delivery device 156. The supplemental gas delivery device 156 may include bridging portions 160 fitted into the ports 159 and extending into the interior of the mask 150, and cannulas 158 for press-fitting over the bridging portions 160. In this embodiment, the supplemental gas delivery device 156 may include two cannulas 158, one placed adjacent each nare of a patient in use. However, this embodiment could be modified to use a single opening adjacent the patient's nares, such as illustrated in FIG. 7. The supplemental gas delivery device 156 may include cannulas 158 shaped to bend to extend upward towards the patient's nares.

Figure 16:
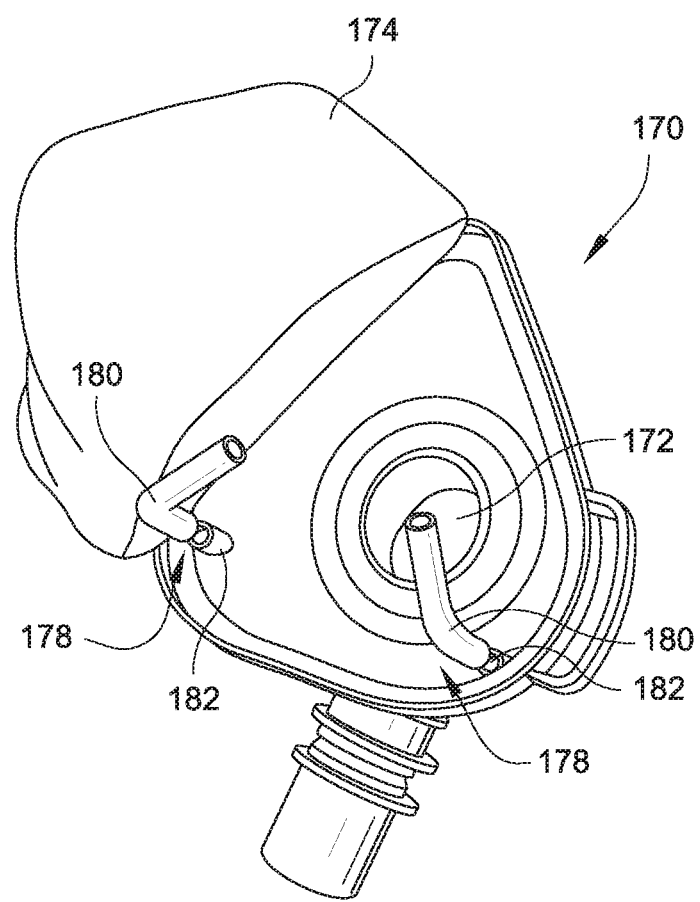
FIG. 16 is a rear perspective view of a known nasal mask assembly retrofitted with a supplemental gas delivery device according to an embodiment of the present invention.
Figure 17:
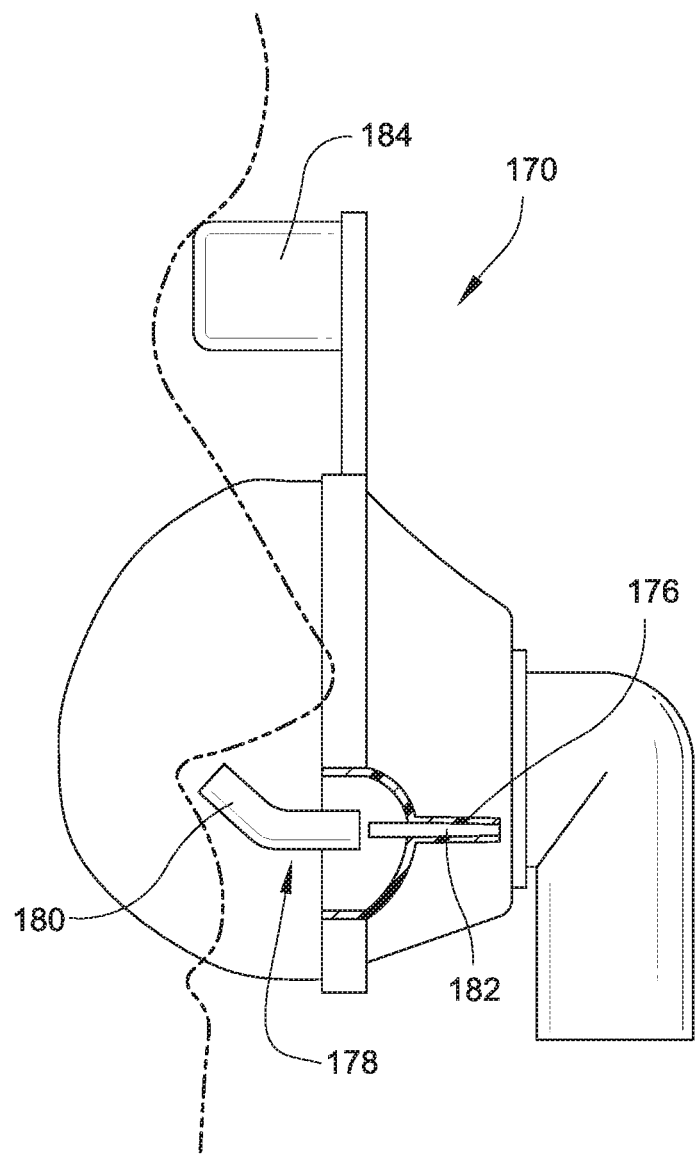
FIG. 17 is a cross-sectional view of the nasal mask assembly of FIG. 16.

FIG. 16 illustrates a known mask 170 (commercially sold as the Philips Respironics Profile™ Lite nasal mask) that includes a cushion 174 (pulled back to expose the interior of the mask assembly) and an inlet tube 172 for delivery of primary breathable gas into the interior of the mask 170. This mask 170 includes two ports 176, as also illustrated in the cross-sectional view of FIG. 17, positioned on both sides and slightly below the inlet tube 172, and a forehead support 184.

The mask 170 may be equipped or retrofitted with a supplemental gas delivery device 178. The supplemental gas delivery device 178 may include bridging portions 182 fitted into the ports 176 and extending into the interior of the mask 170, and cannulas 180 for press-fitting over the bridging portions 182. In this embodiment, the supplemental gas delivery device 178 may include two cannulas 180, one disposed to direct supplemental gas adjacent each nare of a patient in use. However, this embodiment could be modified to use a single opening adjacent the patient's nares, such as illustrated in FIG. 7. The supplemental gas delivery device 178 may include cannulas 180 shaped to bend upwards towards the patient's nares.

Figure 18:
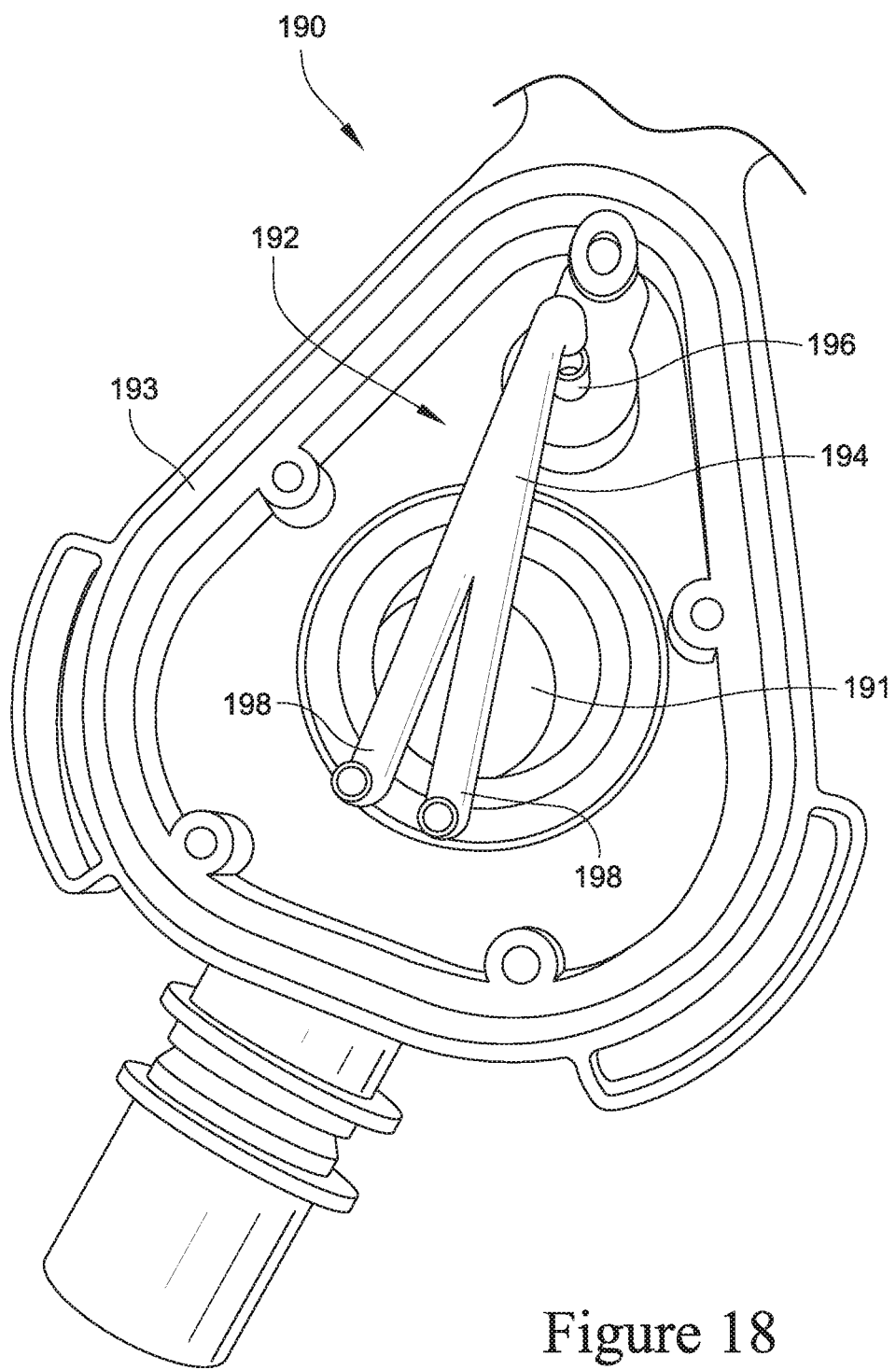
FIG. 18 is a rear perspective view of a known full facial mask assembly retrofitted with a supplemental gas delivery device according to an embodiment of the present invention.
Figure 19:
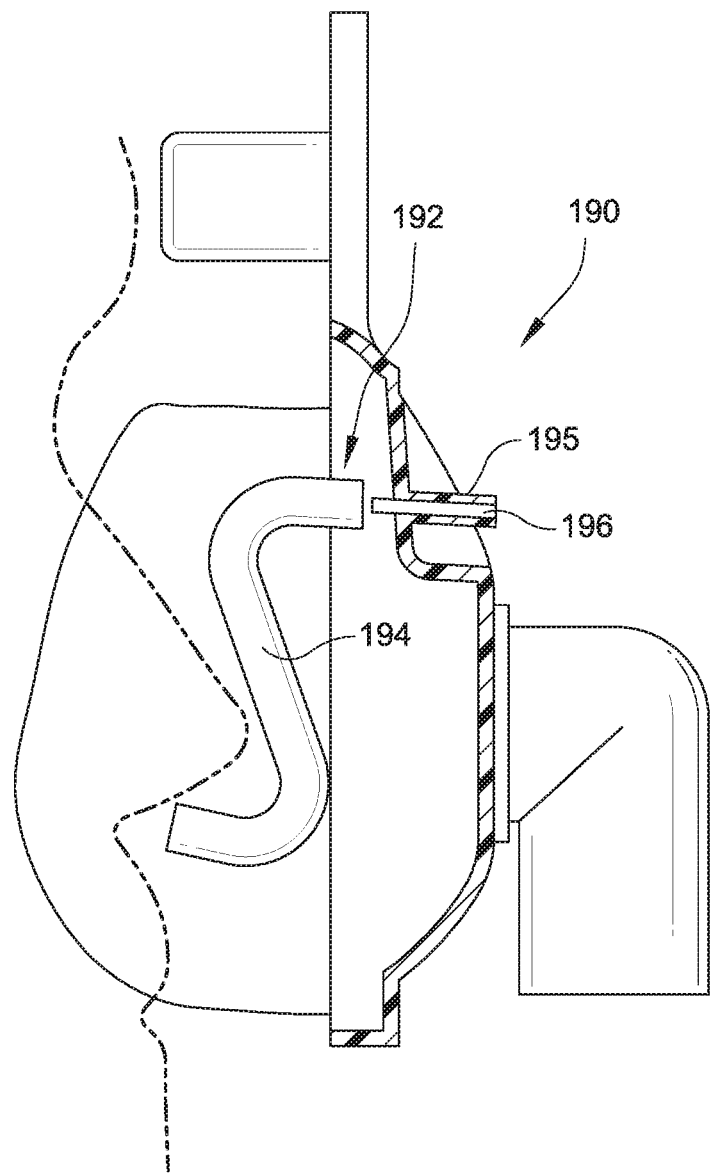
FIG. 19 is a cross-sectional view illustrating the full facial mask assembly of FIG. 18.

FIG. 18 illustrates a known mask 190 (commercially sold as the Philips Respironics Profile™ Lite nasal mask) that includes a frame 193 and an inlet tube 191 for delivery of primary breathable gas into the interior of the mask 190. A nasal mask of this type is the Philips Respironics Comfort-Classic™ nasal mask. This nasal mask includes one port 195, as also illustrated in the cross-sectional view of FIG. 19, positioned above the inlet tube 191, and a cushion (not shown) for interfacing with a face of the patient in use.

The mask 190 may be equipped or retrofitted with a supplemental gas delivery device 192. The supplemental gas delivery device 192 may include a bridging portion 196 fitted into the port 195 and extending into the interior of the mask 190, and a cannula 194 for press-fitting over the bridging portion 196. In this embodiment, the cannula 194 may include one tub-like portion for connecting to the bridging portion 196, and break into two tub-like portions 198, one placed adjacent each nare of a patient in use. However, this embodiment could be modified to use a single opening adjacent the patient's nares, such as illustrated in FIG. 7. The supplemental gas delivery device 192 may be shaped to extend across the primary gas opening 191. Alternatively, the supplemental gas delivery device 192 could be shaped to extend around the primary gas opening 191.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask assembly for providing Non-invasive Positive Pressure Ventilation (NPPV) therapy to a patient to treat sleep disordered breathing (SDB), the mask assembly comprising:
   a frame at least partly forming a cavity, the frame being shaped and dimensioned to cover at least the patient's nose in use, the frame further comprising:
      a vent assembly positioned on the frame and configured to washout gas during therapy;
      a primary gas delivery inlet configured to be connected to an air delivery tube to provide pressurized gas from a primary source to the cavity to pressurize the cavity during therapy; and
      a supplemental gas port configured to be connected to an end of a supplemental gas delivery tube to provide supplemental gas from a supplemental gas source to the cavity to be provided to the patient during therapy;
   a cushion connected to a perimeter of the frame and configured to contact and seal against the patient's face in use;
   headgear removably attached to the frame and configured to hold the frame and the cushion in position on the patient's face in use; and
   a supplemental gas delivery device having a first end and a second end, the first end of the supplemental gas delivery device being removably connected to the supplemental gas port within the cavity to pneumatically communicate with the supplemental gas delivery tube through the supplemental gas port, and the second end of the supplemental gas delivery device being positioned inferior to the vent assembly within the cavity.

2. The mask assembly of claim 1, wherein the second end of the supplemental gas delivery device is configured to be positioned, in use, such that the patient's nares are between the vent assembly and the second end of the supplemental gas delivery device to deliver the supplemental gas to the patient's nares.

3. The mask assembly of claim 1, wherein the frame consists of one supplemental gas port, and
   wherein the first end of the supplemental gas delivery device consists of a single inlet connected to the supplemental gas port.

4. The mask assembly of claim 1, wherein the second end of the supplemental gas delivery device consists of two outlets, the supplemental gas delivery device being shaped and dimensioned to position each of the outlets proximate to a corresponding one of the patient's nares.

5. The mask assembly of claim 1, wherein the frame consists of one supplemental gas port,
   wherein the first end of the supplemental gas delivery device consists of a single inlet connected to the supplemental gas port, and
   wherein the second end of the supplemental gas delivery device consists of two outlets, the supplemental gas delivery device being shaped and dimensioned to position each of the outlets proximate to a corresponding one of the patient's nares.

6. The mask assembly of claim 1, wherein the frame is shaped and dimensioned to cover the patient's nose and mouth in use.

7. The mask assembly of claim 1, wherein the frame is shaped and dimensioned to cover the patient's nose and not cover the patient's mouth in use.

8. The mask assembly of claim 1, wherein the vent assembly comprises a plurality of holes formed through the frame.

9. The mask assembly of claim 1, wherein the supplemental gas port is positioned on the frame such that the supplemental gas delivery device extends in a superior direction from the supplemental gas port towards the patient's nares in use.

10. The mask assembly of claim 1, wherein the supplemental gas port is positioned on the frame such that the supplemental gas delivery device extends in an inferior direction from the supplemental gas port towards the patient's nares in use.

11. The mask assembly of claim 1, wherein the supplemental gas delivery device is configured to be bent into a desired shape by the user.

12. The mask assembly of claim 1, further comprising an elbow assembly connected to the frame at the primary gas delivery inlet, the elbow assembly configured to be connected to the air delivery tube.

13. The mask assembly of claim 1, further comprising a bridging portion that extends from the supplemental gas port into the cavity, and the first end of the supplemental gas delivery device being configured to receive the bridging portion to removably connect the supplemental gas delivery device to the supplemental gas port.

14. A mask assembly for providing Non-invasive Positive Pressure Ventilation (NPPV) therapy to a patient to treat sleep disordered breathing (SDB), the mask assembly comprising:
  a frame at least partly forming a cavity, the frame being shaped and dimensioned to cover at least the patient's nose in use, the frame further comprising:
    a vent assembly positioned on the frame and configured to washout gas during therapy;
    a primary gas delivery inlet configured to be connected to an air delivery tube to provide pressurized gas from a primary source to the cavity to pressurize the cavity during therapy; and
    a supplemental gas port configured to be connected to an end of a supplemental gas delivery tube to provide supplemental gas from a supplemental gas source to the cavity to be provided to the patient during therapy;
  a cushion connected to a perimeter of the frame and configured to contact and seal against the patient's face in use;
  headgear removably attached to the frame and configured to hold the frame and the cushion in position on the patient's face in use; and
  a supplemental gas delivery device having a first end and a second end that are positioned within the cavity, the first end of the supplemental gas delivery device being removably connected to the supplemental gas port to pneumatically communicate with the supplemental gas delivery tube through the supplemental gas port, and the supplemental gas delivery device being shaped and dimensioned such that, in use, the patient's nares are between the vent assembly and the second end of the supplemental gas delivery device to deliver the supplemental gas to the patient's nares.

15. The mask assembly of claim 14, wherein the frame consists of one supplemental gas port, and
  wherein the first end of the supplemental gas delivery device consists of a single inlet connected to the supplemental gas port.

16. The mask assembly of claim 14, wherein the second end of the supplemental gas delivery device consists of two outlets, the supplemental gas delivery device being shaped and dimensioned to position each of the outlets proximate to a corresponding one of the patient's nares.

17. The mask assembly of claim 14, wherein the frame consists of one supplemental gas port,
  wherein the first end of the supplemental gas delivery device consists of a single inlet connected to the supplemental gas port, and
  wherein the second end of the supplemental gas delivery device consists of two outlets, the supplemental gas delivery device being shaped and dimensioned to position each of the outlets proximate to a corresponding one of the patient's nares.

18. The mask assembly of claim 14, wherein the frame is shaped and dimensioned to cover the patient's nose and mouth in use.

19. The mask assembly of claim 14, wherein the frame is shaped and dimensioned to cover the patient's nose and not cover the patient's mouth in use.

20. The mask assembly of claim 14, wherein the vent assembly comprises a plurality of holes formed through the frame.

21. The mask assembly of claim 14, wherein the supplemental gas port is positioned on the frame such that the supplemental gas delivery device extends in a superior direction from the supplemental gas port towards the patient's nares in use.

22. The mask assembly of claim 14, wherein the supplemental gas port is positioned on the frame such that the supplemental gas delivery device extends in an inferior direction from the supplemental gas port towards the patient's nares in use.

23. The mask assembly of claim 14, wherein the supplemental gas delivery device is configured to be bent into a desired shape by the user.

24. The mask assembly of claim 14, further comprising an elbow assembly connected to the frame at the primary gas delivery inlet, the elbow assembly configured to be connected to the air delivery tube.

25. The mask assembly of claim 14, further comprising a bridging portion that extends from the supplemental gas port into the cavity, and the first end of the supplemental gas delivery device being configured to receive the bridging portion to removably connect the supplemental gas delivery device to the supplemental gas port.

* * * * *